United States Patent [19]
Bierman

[11] Patent Number: 5,578,013
[45] Date of Patent: *Nov. 26, 1996

[54] CATHETER ANCHORING SYSTEM

[75] Inventor: Steven F. Bierman, Del Mar, Calif.

[73] Assignee: Venetec International, Inc., Mission Viejo, Calif.

[*] Notice: The term of this patent shall not extend beyond the expiration date of Pat. No. 5,456,671.

[21] Appl. No.: 223,948

[22] Filed: Apr. 6, 1994

Related U.S. Application Data

[63] Continuation of PCT/US94/02994, Mar. 18, 1994, which is a continuation-in-part of Ser. No. 121,942, Sep. 15, 1993, Pat. No. 5,456,671, which is a continuation-in-part of Ser. No. 34,340, Mar. 19, 1993, Pat. No. 5,354,282, which is a continuation-in-part of Ser. No. 695,549, May 3, 1991, Pat. No. 5,314,411, which is a continuation-in-part of Ser. No. 518,964, May 4, 1990, Pat. No. 5,192,273, which is a continuation-in-part of Ser. No. 384,326, Jul. 24, 1989, abandoned.

[51] Int. Cl.$^6$ .................................................... A61M 5/32
[52] U.S. Cl. .................. 604/180; 604/174; 128/DIG. 26
[58] Field of Search .................................. 604/174, 175, 604/176, 177, 178, 179, 180, 283, 905; 128/DIG. 26

[56] References Cited

U.S. PATENT DOCUMENTS

| D. 273,993 | 5/1984 | Schulte et al. . |
|---|---|---|
| D. 302,304 | 7/1989 | Kulle et al. . |
| D. 323,390 | 1/1992 | Paine et al. . |
| 2,525,398 | 10/1950 | Collins . |
| 2,533,961 | 12/1950 | Rousseau et al. . |
| 3,064,648 | 11/1962 | Bujan . |
| 3,167,072 | 1/1965 | Stone et al. . |
| 3,245,567 | 4/1966 | Knight . |
| 3,394,954 | 7/1968 | Sarns . |
| 3,686,896 | 8/1972 | Rutter . |
| 3,766,915 | 10/1973 | Rychlik . |
| 3,856,020 | 12/1974 | Kovac . |
| 3,900,026 | 8/1975 | Wagner . |
| 3,906,946 | 9/1975 | Nordstrom . |
| 3,920,001 | 11/1975 | Edwards . |
| 3,942,228 | 3/1976 | Buckman et al. . |
| 3,973,565 | 8/1976 | Steer . |
| 4,037,599 | 7/1977 | Raulerson . |
| 4,082,094 | 4/1978 | Dailey . |
| 4,114,618 | 9/1978 | Vargas . |
| 4,116,196 | 9/1978 | Kaplan et al. . |
| 4,123,091 | 10/1978 | Cosentino et al. . |

(List continued on next page.)

FOREIGN PATENT DOCUMENTS

| 114677 | 8/1984 | European Pat. Off. . |
|---|---|---|
| 169704 | 1/1986 | European Pat. Off. . |
| 247590 | 12/1987 | European Pat. Off. . |
| 263789A1 | 4/1988 | European Pat. Off. . |
| 356683 | 3/1990 | European Pat. Off. ........ 128/DIG. 26 |
| 367549A3 | 5/1990 | European Pat. Off. . |
| 2341297 | 4/1975 | Germany . |
| 2063679 | 6/1981 | United Kingdom . |
| 2086466 | 5/1982 | United Kingdom . |
| 90/05559 | 5/1990 | WIPO . |
| 91/16939 | 11/1991 | WIPO . |
| 92/03070 | 4/1992 | WIPO . |
| 92/03923 | 5/1992 | WIPO . |

Primary Examiner—Todd E. Manahan
Attorney, Agent, or Firm—Knobbe, Martens, Olson & Bear

[57] ABSTRACT

A catheter anchoring system is provided to securely anchor to a patient's skin a catheter and fluid supply tube interconnection. The anchoring system comprises a retainer configured to receive a catheter adaptor in a variety of positions. The adaptor interconnects the catheter and the fluid supply tube. In one embodiment the adaptor includes a lure-lock fitting to lock onto a hub on the proximal end of the catheter. The anchoring system additionally includes a flexible, adhesive anchor pad which supports a tube clip, as well as the retainer. The retainer includes a channel that is configured to receive the adaptor in a snap-fit manner. The retainer also includes a plurality of lateral slots. Each slot is sized to receive and to capture a radically extending member (e.g., an annular collar) of the adaptor to prevent the adaptor from sliding within the channel.

10 Claims, 10 Drawing Sheets

U.S. PATENT DOCUMENTS

| | | |
|---|---|---|
| 4,129,128 | 12/1978 | McFarlane . |
| 4,133,312 | 1/1979 | Burd . |
| 4,161,177 | 7/1979 | Fuchs . |
| 4,224,937 | 9/1980 | Gordon . |
| 4,250,880 | 2/1981 | Gordon . |
| 4,316,461 | 2/1982 | Marais et al. . |
| 4,326,519 | 4/1982 | D'Alo et al. . |
| 4,362,156 | 12/1982 | Feller, Jr. et al. . |
| 4,392,853 | 7/1983 | Muto . |
| 4,397,647 | 8/1983 | Gordon .......................... 128/DIG. 26 |
| 4,405,163 | 9/1983 | Voges et al. . |
| 4,449,975 | 5/1984 | Perry . |
| 4,453,933 | 6/1984 | Speaker . |
| 4,474,559 | 10/1984 | Steiger . |
| 4,480,639 | 11/1984 | Peterson et al. . |
| 4,516,968 | 5/1985 | Marshall et al. . |
| 4,585,435 | 4/1986 | Vaillancourt . |
| 4,633,863 | 1/1987 | Filips et al. . |
| 4,711,636 | 12/1987 | Bierman . |
| 4,742,824 | 5/1988 | Payton et al. . |
| 4,752,292 | 6/1988 | Lopez et al. . |
| 4,792,163 | 12/1988 | Kulle . |
| 4,795,429 | 1/1989 | Feldstein . |
| 4,826,486 | 5/1989 | Palsrok et al. ................... 128/DIG. 26 |
| 4,834,702 | 5/1989 | Rocco . |
| 4,834,716 | 5/1989 | Ogle, II . |
| 4,838,858 | 6/1989 | Wortham et al. . |
| 4,852,844 | 8/1989 | Villaveces . |
| 4,857,058 | 8/1989 | Payton . |
| 4,863,432 | 9/1989 | Kvalo . |
| 4,880,412 | 11/1989 | Weiss . |
| 4,897,082 | 1/1990 | Erskine . |
| 4,898,587 | 2/1990 | Mera . |
| 4,919,654 | 4/1990 | Kalt . |
| 4,934,375 | 6/1990 | Cole et al. . |
| 4,955,864 | 9/1990 | Hajduch . |
| 4,966,582 | 10/1990 | Sit et al. . |
| 4,976,700 | 12/1990 | Tollini . |
| 4,981,469 | 1/1991 | Whitehouse et al. . |
| 4,997,421 | 3/1991 | Palsrok et al. . |
| 5,037,397 | 8/1991 | Kalt et al. . |
| 5,084,026 | 1/1992 | Shapiro .......................... 128/DIG. 26 |
| 5,192,273 | 3/1993 | Bierman et al. . |
| 5,192,274 | 3/1993 | Bierman . |
| 5,344,414 | 9/1994 | Lopez et al. ............................. 604/283 |
| 5,380,293 | 1/1995 | Grant . |
| 5,380,294 | 1/1995 | Persson . |
| 5,380,301 | 1/1995 | Prichard et al. . |
| 5,382,239 | 1/1995 | Orr et al. . |
| 5,382,240 | 1/1995 | Lam . |
| 5,395,344 | 3/1995 | Beisang, III et al. . |
| 5,413,562 | 5/1995 | Swauger . |

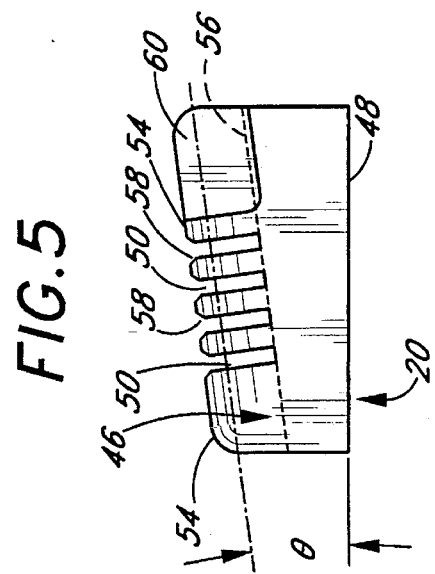
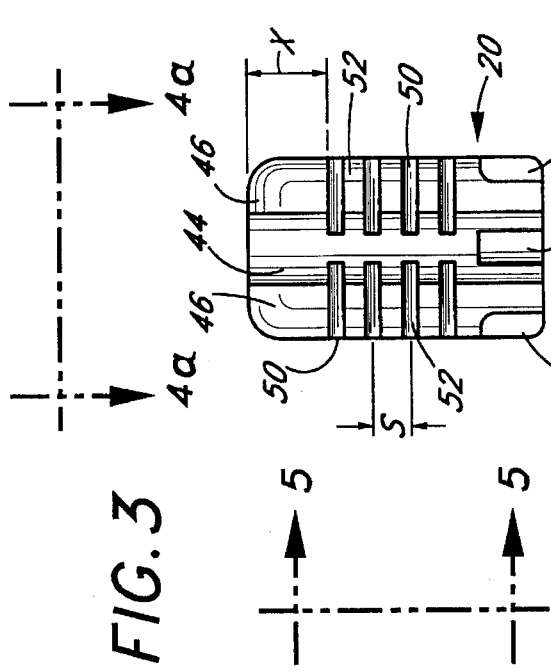
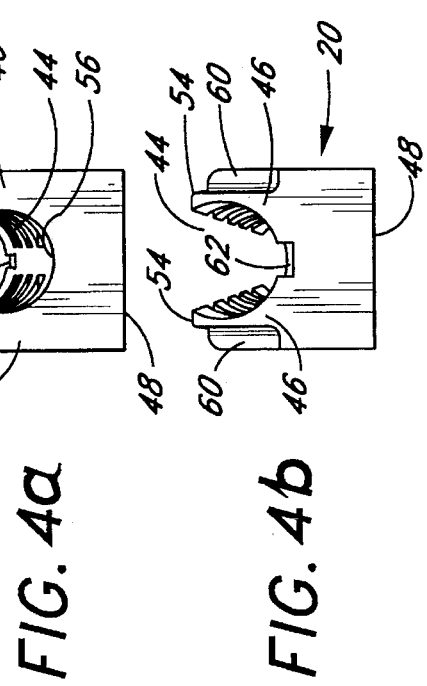

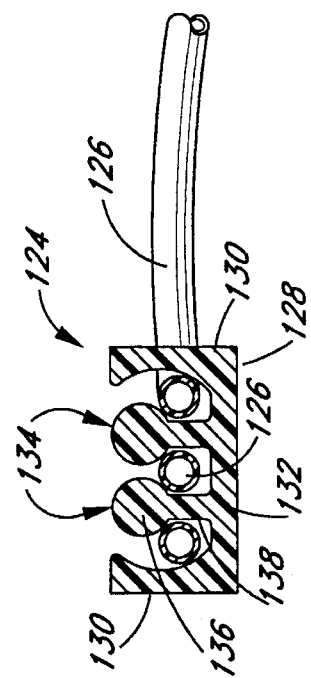
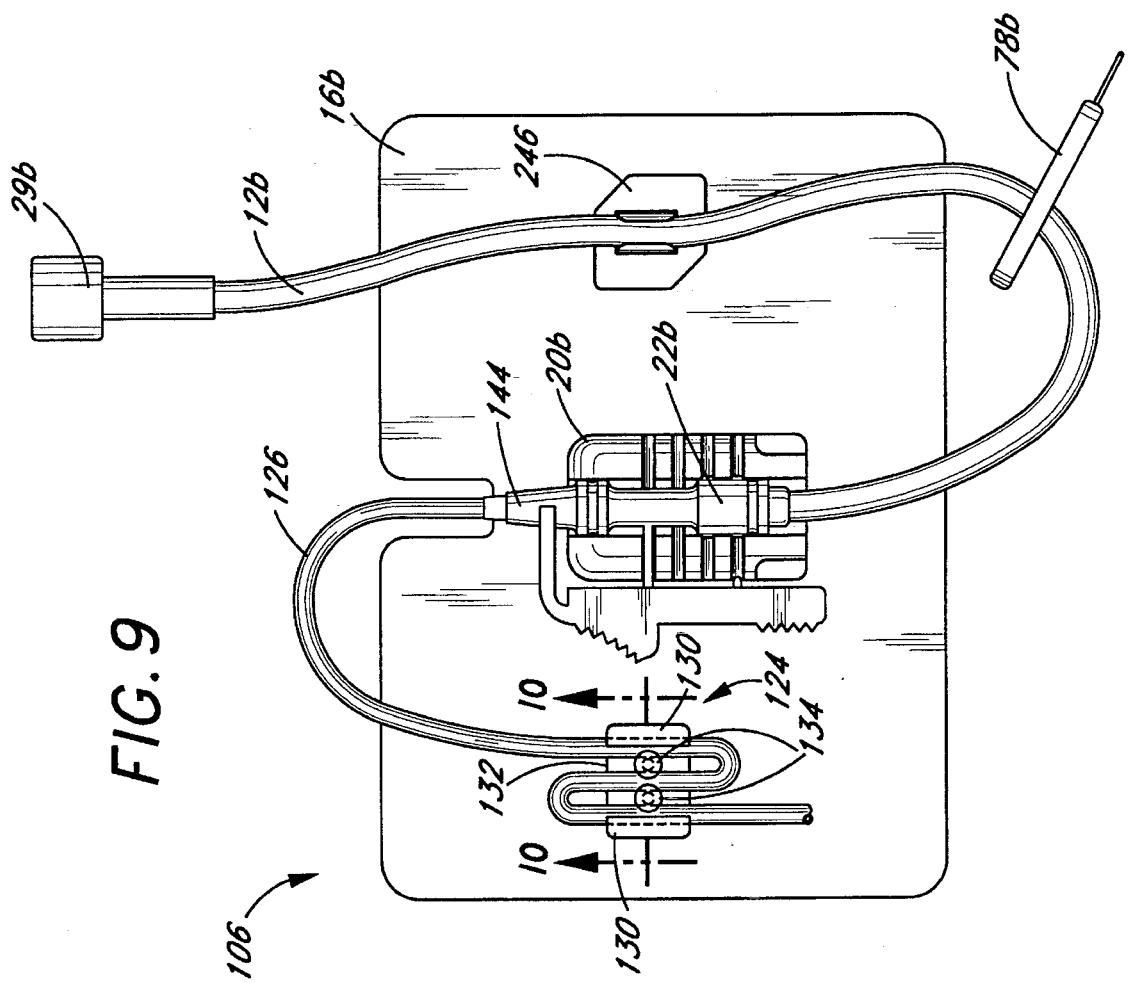

CATHETER ANCHORING SYSTEM

RELATED CASES

This application is a continuation of PCT Application Serial No. PCT/US94/02994, filed Mar. 18, 1994, which designates the United States, and is a continuation-in-part of application Ser. No. 08/121,942, filed Sep. 15, 1993, now U.S. Pat No. 5,456,671 which is a continuation-in-part of application Ser. No. 08/034,340, filed Mar. 19, 1993, now U.S. Pat. No. 5,354,282, issued on Oct. 11, 1994, which is a continuation-in-part of application Ser. No. 07/695,549, filed May 3, 1991, now U.S. Pat. No. 5,314,411, issued on May 24, 1994, which is a continuation-in-part of application Ser. No. 07/518,964, filed May 4, 1990, now U.S. Pat. No. 5,192,273, issued Mar. 9, 1993, which is a continuation-in-part of application Ser. No. 07/384,326, filed Jul. 24, 1989, now abandoned.

BACKGROUND OF THE INVENTION

1. Field of the Invention

The present invention relates in general to a percutaneous catheterization system, and, in particular, to a catheter anchoring system which securely interconnects an indwelling catheter with a tubing and securely anchors such interconnection to a patient's skin.

2. Description of Related Art

Medical treatment of patients commonly involves the use of percutaneously inserted catheters to direct fluids directly into the bloodstream, a specific organ or an internal location of the patient, or to monitor vital functions of the patient. For instance, intra-arteriovenous catheters are commonly used to direct fluids and/or medication directly into the bloodstream of the patient. Epidural catheters are commonly used to direct anesthesia into an epidural space to anesthetize a specific location of the patient. Intervascular catheters are commonly used to monitor arterial blood pressure.

The fluid (e.g., parenteral liquid, medication or anesthesia) typically drains from a container positioned above the patient. The fluid flows through tubing and into an indwelling catheter. The catheter and fluid tubing are commonly removably attached by a conventional lure-type connector, such as the type described in U.S. Pat. No. 4,224,937.

In common practice, a health care provider, such as, for example, a nurse or doctor (for ease of description, as used herein the term "nurse" will refer to health care providers generally and will not be restrictive in meaning), uses adhesive or surgical tape to maintain the catheter in place on the skin of the patient. The connection between the tubing and the catheter is likewise maintained by use of tape.

The nurse may also form a safety loop in the tubing so that any tension applied to the tubing does not directly pass to the catheter cannula, but rather is absorbed by the slack of the safety loop. The nurse typically loosely tapes the loop to the skin of the patient.

This entire taping procedure takes several minutes of the valuable time of the health care provider. Furthermore, nurses commonly remove their gloves when taping because most nurse find such taping procedures difficult and cumbersome when wearing gloves.

The catheterization process often requires frequent disconnection between the catheter and the fluid supply tube. For instance, intravenous catheterization is frequently maintained for several days, depending upon the condition of the patient. The catheter tubing is generally replaced every 24 to 48 hours in order to maintain the sterility of the fluid and the free-flow of the fluid through the tubing. A nurse must thus frequently change the tubing and retape the connection. Moreover, the tape, which secures the catheter to the skin of the patient, often covers the cannula insertion point. The nurse must remove the tape to inspect the insertion point for inflammation or infection, and must then repeat the above-described taping procedure.

A great deal of valuable time is thus used in applying significant amounts of surgical tape to indwelling catheters. The frequent application and removal of surgical tape also commonly results in the excoriation of the skin of the patient in the area of the insertion.

A number of catheterization systems have recently been developed which improve the stabilization of the catheter system and obviate the need for frequent application and removal of surgical tape. One such system is disclosed by U.S. Pat. No. 5,192,273 issued to the present Applicant, which is hereby incorporated by reference.

The '273 patent discloses an adaptor which interconnects the catheter with a fluid supply tubing. The adaptor snaps into a base attached to the patient's skin by an adhesive pad. Specifically, a nurse presses the adaptor between upstanding legs of the base. Detents on the adaptor legs slide into corresponding annular grooves in the adaptor body to hold the adaptor to the base.

Although the base holds the adaptor securely in place, a nurse may have difficulty positioning and aligning the annular grooves of the adaptor with the detents on the base. Exigent circumstances may further exacerbate the difficulties associated with properly positioning the adaptor onto the base. Some nurses and other health care providers may also have trouble determining how to engage the catheter adaptor with the base.

SUMMARY OF THE INVENTION

The catheter anchoring system of the present invention provides an adaptor retainer which is not position or technique sensitive. That is, the nurse simply locates the catheter adaptor generally above the retainer, and presses the adaptor into the retainer. Engagement requires only coarse alignment of the adaptor with the retainer.

In accordance with a preferred embodiment of the present invention, the retainer comprises a pair of opposing longitudinal walls. Each wall defines a series of slots which are laterally aligned with the opposing slots of the opposite side wall. Each slot is sized such that a portion of the catheter adaptor (e.g., a support arm or an annular collar or flange) inserts into at least one slot. So positioned, the adaptor is prevented from moving in a direction generally parallel to a longitudinal direction of the retainer.

The central channel is generally U-shaped and is formed by the arcuate shape of the walls. The channel axis lies, in a vertical plane, generally parallel to the retainer longitudinal axis. The channel is interposed between the opposing longitudinal walls and has a truncated circular cross-sectional shape. The central channel, in cross-section, extends through an arc, which is greater than 180° about the channel axis, such that with the adaptor body positioned within the channel, the longitudinal walls prevent the adaptor from moving either in a lateral direction or in a transverse direction (which are normal to the longitudinal axis of the retainer).

The channel axis and its bottom surface is preferably positioned oblique to the horizontal at an angle substantially equal to an incident angle of the indwelling catheter. This incident angle preferably ranges between 0° and 30°.

In accordance with a further aspect of the present invention, a catheter anchoring system is provided to securely retain a catheter adaptor (which interconnects a catheter and a tubing) on the skin of the patient. The anchoring system comprises a base having a rail extending in a longitudinal direction, and a retainer configured to receive and retain the catheter adaptor. The retainer comprises a groove configured to receive the rail in a manner enabling the retainer to slide over the base. The anchoring system further comprises an interlocking element which prevents the retainer from sliding over the base with the retainer holding the catheter adaptor.

The interlocking element preferably comprises a plurality of teeth and a pawl. The pawl engages the teeth with the retainer holding the adaptor. The pawl desirably extends from a flexible finger which the adaptor deflects when positioned within the retainer.

In accordance with a further aspect of the present invention, a catheter anchoring system comprises a catheter adaptor, a retainer and a base pad which adheres to the skin of a patient and supports the retainer. The catheter adaptor comprises a tubular body connected to a radially extending support arm. The support arm in turn connects to a clip which pivots relative to the tubular body.

The retainer comprises a pair of opposing longitudinal walls. Each wall defines a series of slots. Each slot is sized such that a portion of the support arm of the catheter adaptor extends through the slot. The slot prevents the support arm from moving in a direction generally parallel to a longitudinal direction of the retainer.

The retainer further comprises a central channel which extends through the retainer about an axis which is generally parallel to the longitudinal axis. The channel is interposed between the opposing longitudinal walls and has a truncated circular cross-sectional shape. The central channel, in cross-section, is sized to encompass the tubular body through an angle greater than about 180°.

The anchoring system may additionally comprise a tube clip configured to receive a portion of the tube. The anchoring system may also comprise an S-clip having a plurality of retainers to secure a microbore tubing connected to the tube by the adaptor.

In a preferred embodiment, the anchoring system additionally comprises a base having a rail that extends in the longitudinal direction. The retainer includes a corresponding shaped groove configured to receive the rail. The retainer slides over the base with the rail positioned within the groove.

The anchoring system may also comprise an interlocking element which prevents the retainer from sliding over the base with the retainer holding the adaptor. The interlocking element desirably comprises a series of teeth and a pawl.

In accordance with a preferred method of anchoring a catheter to a patient, a base is positioned proximate to an indwelling catheter. A retainer is slid over the base to locate the retainer in a desired position relative to the indwelling catheter. An adaptor is inserted into the retainer to prevent the adaptor from moving relative to the retainer, and the retainer and base are interlocked to prevent the adaptor from moving relative to the indwelling catheter.

In a preferred embodiment, the adaptor deflects a cantilevered finger as it is inserted into the retainer. The deflection of the finger in turn causes a pawl to engage a series of teeth.

The interengagement between the teeth and pawl prevent the retainer from sliding over the base. With the adaptor removed from the retainer, the retainer freely slides over the base.

The method desirably further includes the steps of attaching the catheter adaptor to the indwelling catheter. The distal end of the adaptor is inserted into the proximal end of the catheter hub which is then engaged by a clip slidably mounted on the adaptor. The clip is slid proximally on the adaptor to grasp the catheter hub. With the clip so positioned, the clip is locked in place to secure the engagement with the catheter hub.

An additional aspect of the present invention provides a catheter anchoring system for securing an indwelling catheter within a body lumen of a patient and for securely interconnecting the indwelling catheter with a tube. The catheter anchoring system comprises a catheter adapter having a generally tubular body defined between distal and proximal ends. The distal end is configured to engage the catheter proximal end and the proximal end is configured to couple to a distal end of the supply tube. The catheter adapter additionally comprises a radially extending member which projects from an exterior surface of the tubular body in a radial direction.

A retainer of the catheter anchoring system comprises a longitudinal channel configured to receive the tubular body of the adapter in a snap fit manner. The retainer additionally comprises a plurality of lateral slots which are sized to receive and to capture the radially extending member of the adapter with the adapter positioned within the channel. The retainer prevents the adapter from sliding in a longitudinal direction when one of the slots receives the radially extending member.

In a preferred embodiment, the radially extending member comprises a support arm which connects a clip to the tubular body. In an alternative preferred embodiment, the radially extending member comprises an annular collar which circumscribes the tubular body.

An additional aspect of the present invention provides a catheter anchoring system comprising an anchor pad. The anchor pad has a laminate structure formed by a cellulose foam layer an adhesive layer. The anchor pad preferably has a roughened or porous upper surface to facilitate attachment of the retainer or tube clip by an adhesive. A woven fiber (e.g., paper may be attached to the foam to form the upper layer. Alternatively, the top surface of the foam layer may be corona treated to form the upper surface.

The anchor pad generally has a trapezoidal shape defined by parallel distal and proximal edges. The distal edge has a length longer than the proximal edge. A notch extends into the anchor pad from the distal edge and has a sufficient size such that a health care provider can visually inspect the catheter cannula with an anchor pad position about the catheter.

The anchor pad may preferably include indicia (e.g., arrow, figure, words, etc.) which identify the desired direction of orientation of the anchor pad with respect to the indwelling catheter. The anchor pad preferably has rounded corners and the longitudinal side edges have concave configurations. The anchor pad desirably supports a retainer which receives a catheter adapter. The retainer is preferably aligned with the notch of the anchor pad.

In accordance with a preferred method of anchoring an indwelling catheter/tube interconnection to a patient, an adapter is provided having a generally tubular body with a radially extending member. An anchor pad is also provided with an adhesive back. The anchor pad supports a retainer configured to receive the adapter and has a series of lateral slots. The anchor pad is attached to the patient's skin proximate to an indwelling catheter. The radially extending member of the adapter is positioned above the series of slots. The retainer is deflected so as to open the channel to a size sufficient to receive the adapter, and the adapter is inserted into the channel. The radially extending member is inserted into one of the slots. The retainer is then permitted to spring back to an undeflected position such that the tubular body is captured within the retainer.

Another method of the present invention comprises the steps of providing an anchor pad which supports the retainer. The retainer is configured to receive a catheter adapter. The anchor pad has a trapezoidal shape formed by a longer distal edge and a shorter proximal edge. The anchor pad further includes an adhesive backing. The anchor pad is positioned over the patient's skin such that the shorter proximal side is generally adjacent to the indwelling catheter. The anchor pad is adhered to the patient's skin.

An additional aspect of the invention involves an anchoring system for a catheter. The anchoring system includes an adaptor which has a generally tubular body with a distal end. The distal end of the adaptor is configured to engage a proximal end of the catheter. The distal end also includes a lure-lock connector which is adapted to engage a corresponding lure-lock connector of the catheter proximal end. The adaptor additionally includes a radially extending member which projects from an exterior surface of the adaptor body in a radial direction and at a point which is distanced from the lure-lock connector of the adaptor distal end.

The anchoring system also includes a retainer. The retainer includes a channel that is configured to receive the body of the adaptor. The retainer also includes a plurality of longitudinal slots. Each slot is sized to receive and to capture the radially extending member of the adaptor with the adaptor positioned within the channel of the retainer. In this manner, the adaptor is prevented from sliding within the retainer channel.

BRIEF DESCRIPTION OF THE DRAWINGS

These and other features of the invention will now be described with reference to the drawings of preferred embodiments which are intended to illustrate and not to limit the invention, and in which:

FIG. 3 is a top plan view of a retainer of the catheter anchoring system of FIG. 2;

FIG. 4a is a front elevational view of the retainer of FIG. 3;

FIG. 4b is a rear elevational view of the retainer of FIG. 3;

FIG. 5 is a side elevational view of the retainer of FIG. 3;

FIG. 8 is a cross-sectional view of the retainer and rail assembly taken along line 8—8 of FIG. 7a;

FIG. 9 is a top plan view of a catheter anchoring system in accordance with an additional preferred embodiment of the present invention;

FIG. 10 is a side elevational view of an S-clip of the catheter anchoring system of FIG. 9 taken along line 10—10;

DETAIL DESCRIPTION OF PREFERRED EMBODIMENTS

Figure 1:
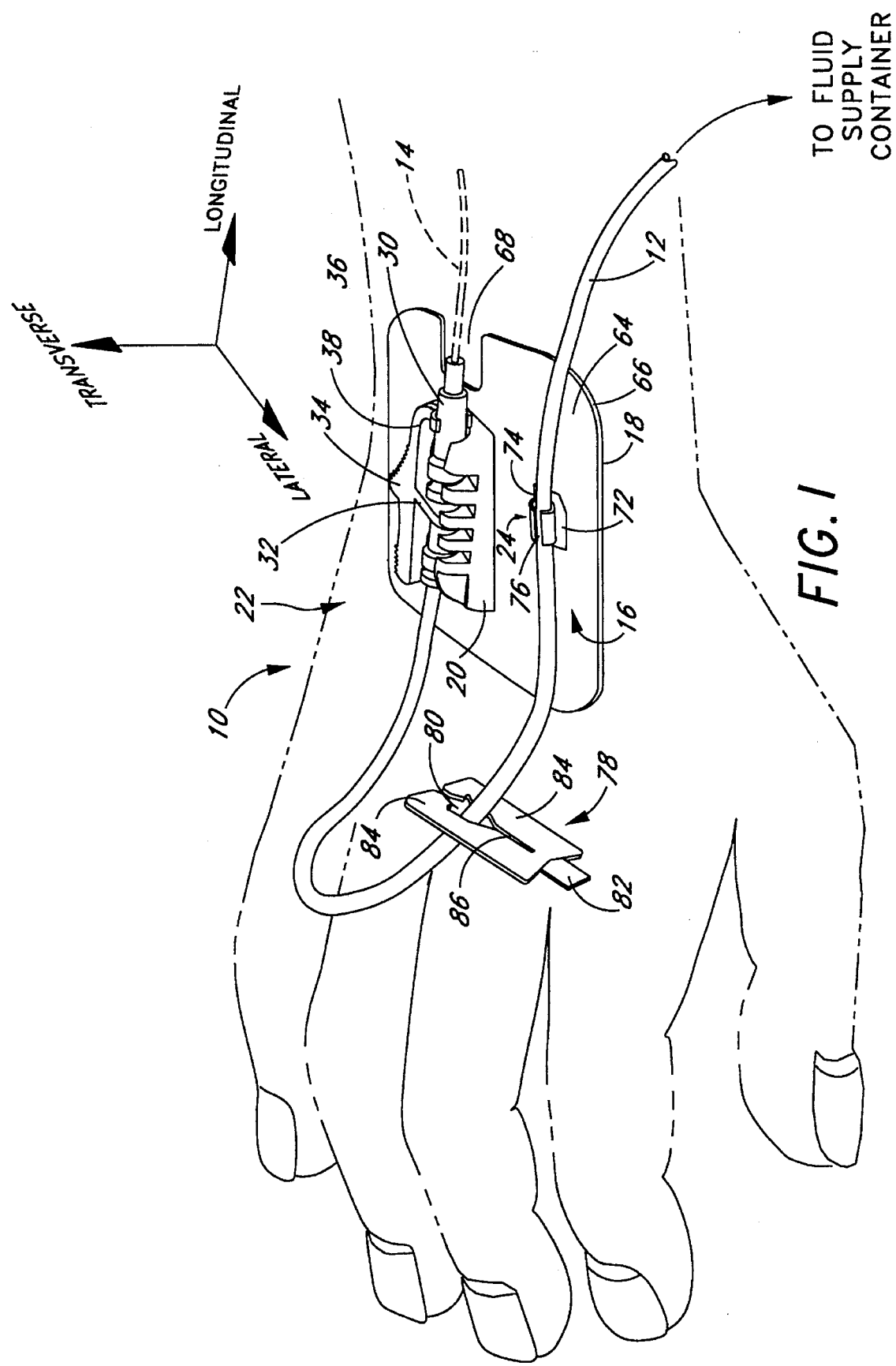
FIG. 1 is a perspective view of a catheter anchoring system in accordance with a preferred embodiment of the present invention, mounted on the back of a patient's hand.

FIG. 1 illustrates in perspective view a catheter anchoring system 10 in accordance with the present invention. The anchoring system 10 securely connects a tube 12 (e.g., a fluid supply tube) to an indwelling catheter 14 and maintains the catheter 14 in the desired indwelling position. The anchoring system 10 is designed for rapid attachment to the catheter 14 and to the patient, without requiring precise alignment or positioning of the components of the anchoring system 10.

Moreover, sturdy anchoring of the catheterization system is achieved without the use of surgical tape. For most catheterization, the anchoring system is attached to the patient only once. Although the fluid supply tubing 12 may be replaced every 24 to 48 hours for intravenous catheterization, the components of the anchoring system 10 attached to the patient remains in place. Thus, surgical tape need not be applied and removed from the patient's skin on multiple occasions.

The catheter anchoring system 10 principally comprises a flexible pad 16 having an adhesive bottom side 18 which attaches to the skin of a patient when used. The pad 16 supports a retainer 20. The retainer 20 is configured to receive and secure in place a catheter adaptor 22 which interconnects the hub 30 of an indwelling catheter 14 and the fluid supply tube 12 connected to a fluid supply container (not shown). The container maintains the fluid to be dispensed to the patient which is fed either by gravity or by pressure. A clamp (not shown) may be used to regulate the fluid flow through the tubing 12. The pad 16 may also support a tubing clip 24 which is used to retain a portion of tubing 12.

Although FIG. 1 illustrates the catheter anchoring system located on the back of a patient's hand (illustrated in phantom lines), it is contemplated that the present invention may be used for catheterization in other locations on the patient's body. For instance, the anchoring system may be used on the medial side of the wrist in connection with a radial artery. The anchoring system 10 may also be used for epidural catheterization, as discussed in detail below, and thus located on the anterior or posterior of the patient's torso.

FIG. 1 illustrates a longitudinal axis, a transverse axis and a lateral axis in relation to the catheter anchoring system 10 to facilitate the following description. Additionally, as used herein, "the longitudinal direction" refers to a direction substantially parallel to the longitudinal axis. "The lateral direction" and "the transverse direction" are in reference to the lateral axis and transverse axis, respectively. Also, "proximal" and "distal" are in reference to the proximity of the fluid supply container attached to the tube 12 (see FIG. 1). The individual components of the catheter anchoring system 10 will now be described in detail.

Catheter Adaptor

Figure 2:
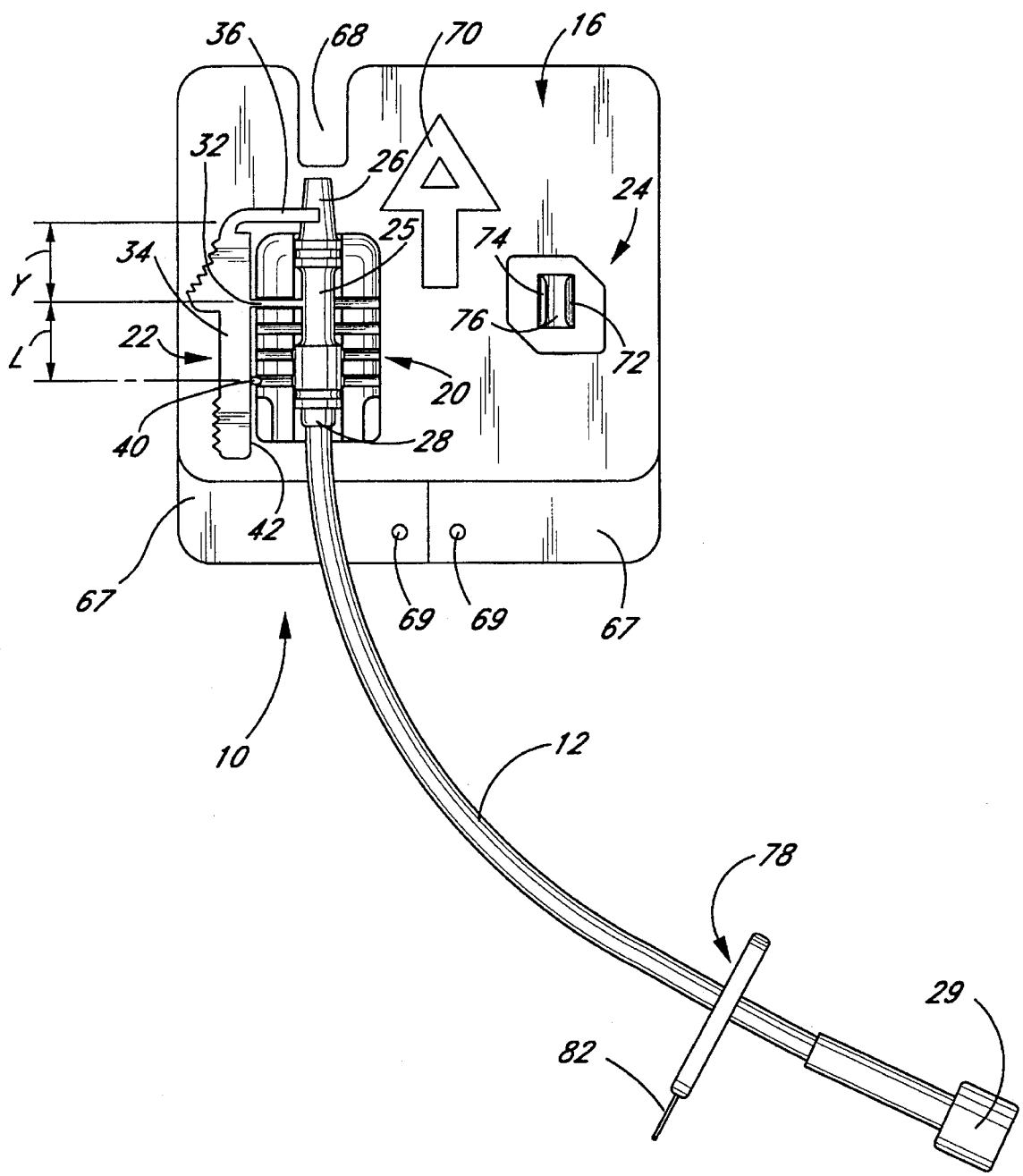
FIG. 2 is a top plan view of the catheter anchoring system of FIG. 1.

FIG. 1 illustrates the catheter adaptor 22 interconnected with a catheter 14. FIG. 2 illustrates the catheter adaptor 22 disconnected from catheter 14. Although these figures illustrate the adaptor 22 as the type disclosed in U.S. Pat. No. 5,193,273, it is contemplated that other types of adaptors can be used as well with the present catheter anchoring system 10. For instance, the catheter adaptor 22 could be a lure-type adaptor, such as the type illustrated by FIG. 11 and described below, or a lure-lock type catheter adaptor 22, such as the type illustrated by FIG. 14 and described below. It is contemplated that those skilled in the art could readily select the type of catheter adaptor 22 to be used with the present catheter anchoring system 10 depending on the particular application (e.g., venous, arterial, epidural, peripheral, etc.) of the anchoring system 10.

As best seen in FIG. 2, the adaptor 22 comprises a tubular body 25 defined between a distal end 26 and a proximal end 28. The proximal end 28 is adapted to receive a distal end of the tube 12. In an exemplary embodiment, at least a portion the fluid supply tube is permanently attached to the body proximal end 28. As shown in FIG. 2, the proximal end of the tubing may then include a standard lure-type connector 29 to connect into a fluid supply line 12.

The distal end 26 is configured to engage the proximal hub 30 of the catheter 14 (see FIG. 1) or any lure-type connector. Although FIG. 2 illustrates the distal end of the adaptor 22 as having a frusto-conical shape configured to engage a standard lure-type catheter hub 30, it is contemplated that the distal end 26 could be configured as well to engage other types of catheter connectors, such as, for example, a Toughy-Bourst adaptor.

A support arm 32 extends outwardly from the tubular body 25 in cantilever fashion. The support arm 32 supports, on a radially outer end of the arm 32, a clip support element (not shown) that extends generally parallel to and is spaced from a longitudinal axis of the tubular body 25.

FIG. 2 further illustrates a clip 34 of the catheter adaptor. The clip 34 attaches to and slides over the clip support element in the longitudinal direction. The clip 34 includes a distal latch 36 which has a generally forked shape to engage a outer surface of the catheter hub 30 distal of a hub collar 38 (see FIG. 1) to securely attach the adaptor 22 to the catheter hub 30.

Interengaging structure (not shown) between the clip support element and the clip 34 permits the clip 34 to slide in the proximal direction, but prevents the clip 34 from sliding in the distal direction. The interengaging element desirably comprises a series of ratchet teeth (not shown) disposed up on upper surface of the clip support element and a pawl (not shown) connected to the clip 34. The pawl extends from the clip 34 in a cantilever fashion and engages the ratchet teeth to prevent distal movement of the clip, as discussed in detail in U.S. Pat. No. 5,193,273, which has been incorporated by reference.

The tubular body 25, the support arm 32 and the clip support element are preferably integrally formed of molded plastic, such as, for example, a clear polycarbonate, so as to be generally stiff, but somewhat flexible. The support arm 32 desirably has enough elasticity to bend. Depressing the proximal end of the clip 34 towards the tubular body 25 moves the latch 36 of the clip 34 away from the tubular body 25. In this manner, the clip 34 pivots about the tubular body 25.

With reference again to FIG. 2, the clip support element desirably comprises a protuberance 40 positioned on an inner surface 42 of the clip support element, proximate to the proximal end of the clip 34. The protuberance is spaced from the support arm by a distance L. The protuberance 40 prevents the clip 34 from pivoting when secured by the retainer 20, as discussed below in detail. The protuberance 40 also limits the degree of deflection of the support arm 32 to reduce fatigue, as fully explained in U.S. Pat. No. 5,193,273, which has been incorporated by reference.

Retainer for Catheter Adaptor

FIGS. 3 through 5 illustrate the retainer 20. The retainer 20 has a generally parallelepiped shape defining a central channel 44 interposed between a pair of opposing longitudinal walls 46. The central channel 44 extends through the retainer 20 along an axis which is generally parallel to the longitudinal axis of the retainer.

As best seen in FIG. 4, the central channel 44 has a generally circular cross-sectional shape which is truncated at a upper end to form a generally U-shaped channel having an upper opening 47. The central channel 44 has a diameter sized to receive the tubular body 25 of the catheter adaptor 22. In a preferred embodiment, the diameter of the central channel 44 generally matches that of the tubular body 25 or is slightly larger.

In cross-section, the central channel 44 extends through an arc greater than 180° about the channel axis such that the transverse length of the opening 47 is less than the diameter of the central channel 44. In an exemplary embodiment, the central channel 44 extends through an arc of about 200° about the channel axis.

FIG. 5 illustrates the channel axis which is desirably skewed relative to a base surface 48 of the retainer 20. An incident angle θ formed between the base surface 48 and the channel axis is less than 45°. The incident angle θ desirably ranges between 0° and 30°. In an exemplary embodiment for intravenous use, the angle θ preferably equals approximately 70. In another exemplary embodiment for arterial use, the incident angle θ preferably equals about 22°. In a further exemplary embodiment, for peripherally inserted central catheters (PICC), the incident angle θ preferably equals 0°.

The longitudinal walls 46 are substantially identical. Each wall 46 has a thickness measured in the lateral direction less than the length of the support arm 32. The wall 46 is thus interposed between the tubular body 25 and the clip 34 when the tubular body 25 is inserted into the central channel 44. The length of each wall 46, measured in the longitudinal direction, is preferably coextensive with the length of the retainer 20.

Each wall 46 comprises a uniform series of slots 50. The series comprises at least two (2) slots 50, and not more than twenty (20) slots 50. More preferably, the series comprises less than seven (7) slots 50. In an exemplary embodiment, as illustrated in the figures of the application, the series comprises four (4) slots 50.

Each slot 50 is sized to receive the support arm 32 of the catheter adaptor 22 to prevent longitudinal displacement of the adaptor 22, as discussed in detail below. Each slot 50 desirably has a rectangular shape. As seen in FIG. 3, the slots 50 extend from an exterior surface 52 through the wall 44, and open into the central channel 44. The width of each slot 50 (measured longitudinally) is desirably slightly greater than the width of the support arm 32, measured in the longitudinal direction to receive the support arm 32, as discussed below.

As illustrated by FIG. 5, each slot 50 has a height as measured in the transverse direction between an upper edge 54 of the longitudinal wall 46 and the bottom 56 of the central channel 44. The height of the slot 50 desirably equals approximately the width of the support arm 32 such that the support arm 32 does not protrude from the retainer 20 in the transverse direction.

The spacing S between the slots 50, on center, desirably equals about half the distance L (see FIG. 2) between the support arm 32 and the protuberance 40 of the catheter adaptor 22.

As FIG. 3 illustrates, a distance X between the most distal slot 50 and the distal end of the retainer 20 is less than the longitudinal distance Y (see FIG. 2) between the support arm 32 and the latch 36 positioned in its most proximal position. This spacing enables the support arm 32 to rest in the most distal slot 50 with the latch 36 retaining a catheter hub 30 distal of the retainer distal end.

FIG. 5 illustrates the upper edge 50 of the longitudinal wall 46 which comprises a series of chamfers 58, each of which slopes into a slot 50. That is, the portion of upper edge 50 of the longitudinal wall 46 which surrounds a slot 50 includes a pair of chamfers 58, with one chamfer 58 located on either side of the slot 50. The chamfers 58 slope downward toward the slot 50 to facilitate the insertion of the support arm 32 of the catheter adaptor 22 into the slot 50, as discussed below.

As shown by FIGS. 3 and 5, each longitudinal wall 46 further comprises a relief 60 disposed on the proximal end of the retainer 20. The relief 60 is sized to receive the protuberance 40 of the adaptor 22. The depth of the relief 60 measured in the lateral direction desirably is slightly greater than the height of the protuberance 40 (i.e., the distance by which the protuberance protrudes from the inner surface 42).

The relief 60 is spaced in the longitudinal direction from the most proximal slot 50 by a distance approximately equal to the spacing S between the slots 50. Thus, the protuberance 40 rests in the relief 60 with the support arm 32 positioned in either of the two most proximal slots 50, as discussed in detail below.

FIGS. 3 and 4 illustrate a key-way groove 62 of the retainer 20. The key-way groove 62 facilitates the removal of the catheter adaptor 22 from the retainer 20, as discussed below in detail. The key-way groove 62 lies at the proximal end of the retainer 20. The key-way groove 62 extends into the retainer 20, and toward the retainer base surface 48 from the bottom surface 56 of the central channel 44. The key-way groove 62 has a transverse width less than the diameter of the central channel 44, and more preferably has a width approximately equal to two-thirds the diameter of the central channel 44. The longitudinal length of the key-way groove 62 desirably equals approximately the longitudinal length of the recesses 60 in the longitudinal walls 46.

The retainer 20 is made of relatively stiff plastic material (e.g., polycarbonate), but is somewhat flexible such that the adaptor 22 forces the upper edges 54 of the longitudinal walls 46 outwardly when a nurse presses the adaptor 24 into the central channel 44 of the retainer 20. When the adaptor 22 sits in the central channel 44, the upper edges 54 of the walls 46 snap inwardly to their original position to securely hold the adaptor 22 within the retainer 20.

An adhesive attaches the retainer 20 to base pad 16. Alternatively, the retainer 20 may be attached to the base pad 16 by like means (e.g., embedding or otherwise weaving the retainer 20 into the base pad 16) as well.

Base Pad

As illustrated by FIG. 1, the flexible base pad 16 comprises a laminate structure comprising an upper paper or other woven or non-woven cloth layer 64, an inner cellulose foam layer 66, and the bottom adhesive layer 18. Alternative, the flexible base pad 16 may comprise an adhesive bottom layer and an upper cellulose foam layer. An upper surface of the foam layer is roughened by corona treating the foam with a low electric charge, as known in the art. The roughened or porous upper surface of the base pad 16 improves cyano-acrylate (or other types of adhesive) adhesion when attaching the retainer 20 to the pad 16.

A removable paper or plastic backing (not shown) desirably covers the bottom adhesive layer 18 before use. The backing preferably resists tearing and is divided into a plurality of pieces to ease attachment of the pad 16 to the patient's skin, as explained below. Desirably, the backing is split along the center line of the flexible base pad 16 in order to expose only half of the adhesive bottom surface 18 at one time. The backing also advantageously extends beyond at least one edge of the base pad 16 to ease removal of the backing from the adhesive layer 18.

As seen in FIG. 2, one or more tabs 67 may be attached to a portion of the backing which extends beyond the flexible base pad 16. In an exemplary embodiment, the tabs 67 have the same laminate structure as the flexible base pad 16. The tabs 67 also can be formed by the paper backing extending beyond the edge of the base pad 16. The tab 67 may also include indicia 69 in the form of dots, words, figures or the like to indicate the placement of fingers when removing the backing from the base pad 16.

A nurse grips the tab 67, preferably at the location of the indicia 69, and peels the backing off one half of the bottom adhesive layer 18. The nurse then places the bottom layer 18 against the patient's skin to adhere the base pad 16 to the patient. Light pressure over the upper layer 64 assures good adhesion between the base pad 16 and the patient's skin. The base pad 16, due to its flexibility, conforms to the contours of the topical surface to which the base pad 16 adheres. The nurse then repeats this procedure for the other half of the pad 16. Alternatively, the nurse may completely remove the backing from the pad 16 before attaching the pad 16 to the patient's skin.

The base pad 16 desirably comprises a notch 68 positioned distal of the location of the retainer 20 on the pad 16 and adjacent to the point of insertion of the catheter cannula. The notch 68 is sized to permit visual inspection of the catheterized site.

As seen in FIG. 2, the base pad 16 desirably may comprise indicia 70 in the form of an arrow which indicates the proper orientation of the base pad 16 in reference to catheterized site. Although the figures illustrate the indicia in the form of an arrow, it is contemplated that other forms of indicia, such as, for example, words or other graphics, could be used as well. In proper use, as illustrated in FIG. 1, the indicia 70 should point in the proximal direction, towards the indwelling catheter 14, or otherwise indicate the proper locate of the pad 16 in reference to the indwelling catheter 14.

In an exemplary embodiment, the laminate structure of the base pad is preferably formed by rolling a paper tape, such as a micro-porous rayon tape, available commercially as MICRO-PORE tape from 3M (Item No. 1530), over a medical grade polyvinyl chloride foam tape, such as that available commercially from 3M (Item No. 9777L). The foam tape preferably includes the bottom liner or backing. The base pad 16 and the tabs 67 are then stamped out of the laminated sheet of foam and paper. The backing between the tabs and the base pad, however, is desirably not severed such that the tabs 67 remain attached to the backing covering the adhesive section 18 of the base pad 16. The backing is then cut into two pieces along the center line of the pad 16 and between the tabs 67.

Tube Clip

FIGS. 1 and 2 illustrate the tube clip 24. The clip 24 secures the fluid supply tube 12 to form a safety loop, as known in the art.

Figure 6:
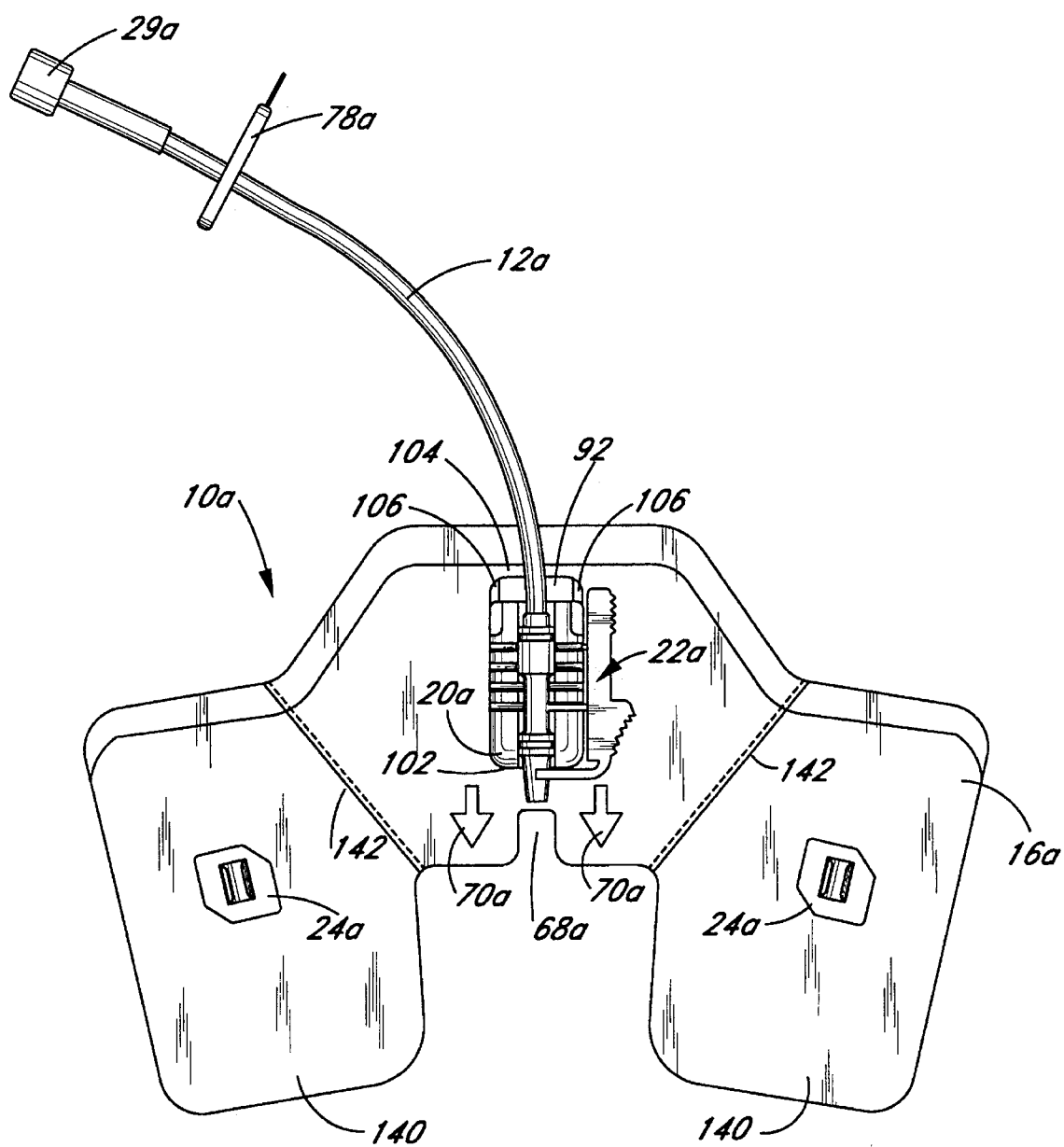
FIG. 6 is a top plan view of a catheter anchoring system in accordance with another preferred embodiment of the present invention.

The tube clip has a plate-like base 72 adhered to or embedded in the base pad 16. The tube clip 24 may be located on the base pad 16 on either side of the retainer 20 to accommodate left hand or right hand mounting. As illustrated in FIG. 6, the anchoring system 10 may further include a second tube clip 24 located on the other side of the retainer 20 from the first tube clip 24.

The clip 24 defines a channel 74 having a generally circular cross-sectional configuration truncated to form an upper orifice 76. The diameter of the channel 74 is desirably slightly less than that of the fluid supply tube 12 so as to ensure a secure interconnection. The channel 74 receives a portion of the fluid supply tube 12 through the orifice 76 upon application of gentle pressure or by pulling the tubing 12 across and through the orifice 76 of the tube clip 24, as explained below. The clip 24 surrounds a substantial portion of the tubing 12 with the tubing 12 positioned within the channel 74.

As seen in FIG. 2, the upper edge of the channel includes tapered ends 77 at the proximal and distal ends of the clip 24. Each tapered end 77 forms a smooth transition between the side edge of the channel 74 and the upper edge, and tapers in lateral width from the side edge toward the center of the tube clip 24. The tapered ends 77 help guide the fluid supply tube 12 into the channel 74 when a nurse pulls the tube across the clip 24. Thus, the nurse does not have to pinch the tube 12 to insert it into the clip 24. Also, the nurse's gloves do not get stuck in the clip 24 when inserting the tube 12, as is typically the case where the nurse is required to pinch the tube 12 to insert it into the clip 24.

Slide Clamp

As illustrated in FIGS. 1 and 2, the catheter anchoring system 10 desirably additionally includes a slide clamp 78 to regulating fluid flow through the tubing, as known in the art. The clamp 78, at one end, includes an aperture 80 which receives the fluid supply tube 12, and, at the opposite end, includes a tab 82. The clamp 78 has a generally forked shape formed by a pair of prongs 84 which defines the aperture 80. The tube 12 snaps between the prongs 84 and into the aperture 80, which has a diameter slightly larger that the fluid supply tube 12.

The prongs 84 converge together in the direction towards the tab 82 to form a tapering slot 86 which opens into the aperture 80. The prongs 84 pinch the tube 12 closed with the tube 12 positioned in the slot 86 so as to block fluid flow therethrough. The clamp 78, however, slides over the tube 12 with the tube 12 positioned through the aperture 80.

The tab 82 desirably has a rectangular shape which generally corresponds the to shape of the key-way groove 62 of the retainer 20. The tab 82 preferably has a thickness greater than that of the distal end of key-way groove 62, measured in the transverse direction, so as to pry the adaptor 22 from the retainer 20. As explained in detail below, the tab 82 may be used to remove the catheter adaptor 22 from the retainer 20.

Retainer Location Adjustment Mechanism

Figure 7B:
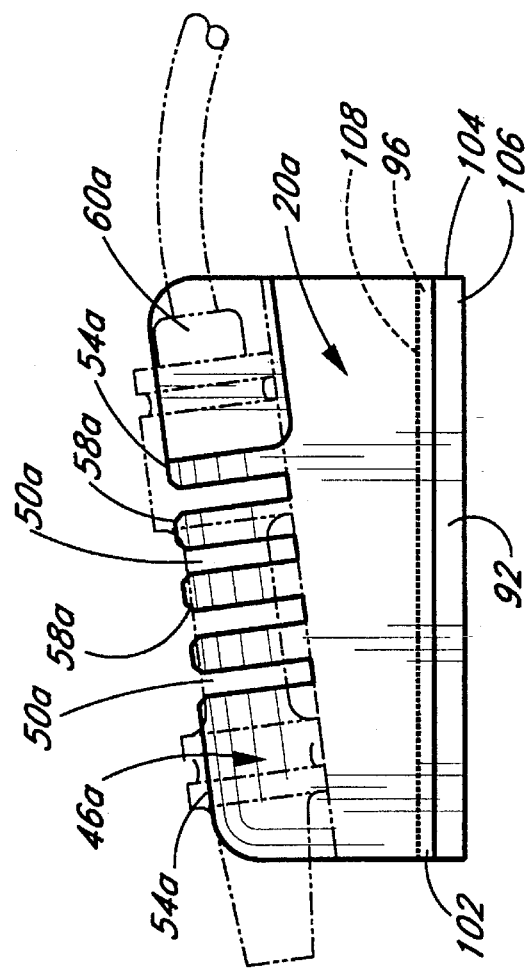
FIG. 7b is a side elevational view of the retainer and rail assembly of FIG. 6.
Figure 7A:
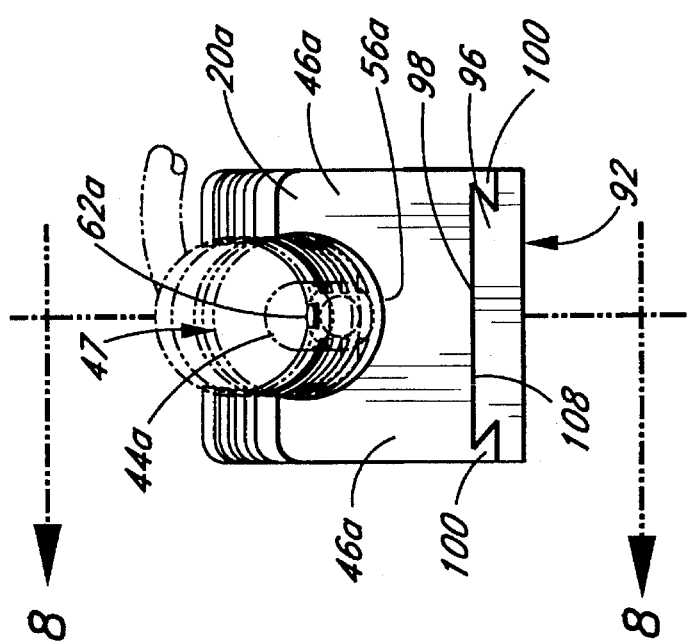
FIG. 7a is a front elevational view of a retainer and rail assembly of the catheter anchoring system of FIG. 6.
Figure 8:
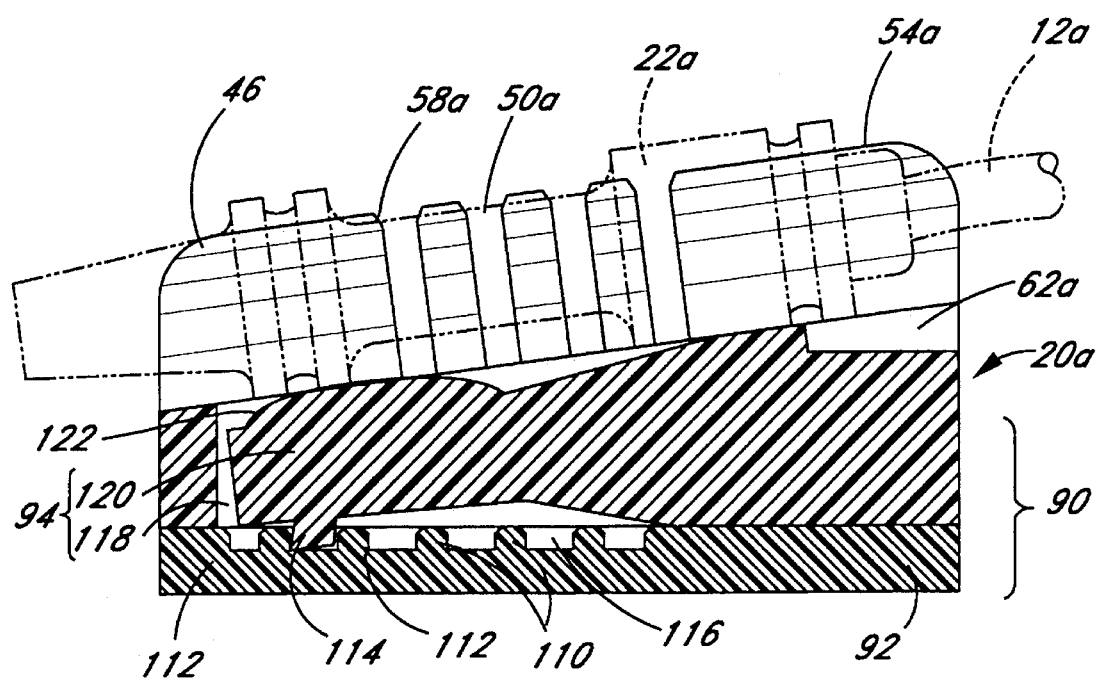

FIG. 6 through 8 illustrate a catheter anchoring system 10a in accordance with another preferred embodiment of the present invention. Where appropriate, like numbers with an "a" suffix have been used to indicate like parts of the two embodiments for ease of understanding.

The catheter anchoring system 10a is substantially identical to the above-described anchoring system 10, with the addition of a retainer location adjustment mechanism 90.

As best seen in FIG. 8, the location adjustment mechanism 90 comprises a base 92 and interlocking mechanism 94 which interconnects the base 92 and the retainer 20a. The retainer 20a slides over the base 92 and the interlocking mechanism 94 secures the retainer 20a to the base 92 at various longitudinal positions. The adjustment mechanism thus allows for precise positioning of the retainer 20 relative to the catheter 14 after the pad 16 is attached to the patient's skin.

The base 92 has a generally parallelepiped shape and comprises a rail 96. FIG. 7a best illustrates that the rail 96 desirably has a "dove-tail" configuration in cross section. That is, the rail 96 has a cross-sectional shape with a flat upper edge 98 and a pair of opposing side edges 100, each edge 100 being angled inward from the upper edge 98 toward the middle of the rail 96. The rail 96 extends along the longitudinal length of the base 92 from the distal end 102 of the base 92 to a point just short of the base proximal end 104. The base 92 includes a pair of stops 106 at the proximal end 104 which close off the proximal end of the rail 96.

An adhesive attaches the base 92 to base pad 16a. Alternatively, the base 92 may be attached to the base pad 16a by like means (e.g., embedding or otherwise weaving the base 92 into the base pad 16a) as well.

The retainer 20a, configured in accordance with the above-description, additionally comprises a groove 108 having a cross-sectional shape corresponding to that of the rail 96. The retainer groove 108 receives the base rail 96 in a manner permitting the retainer 20a to slide over the base 92, but preventing the retainer 20a from moving in the transverse direction away from the base 92. The base stops 106 also limit the retainer's longitudinal travel in a proximal direction.

The interlocking mechanism 94 comprises a plurality of teeth 110 disposed on an upper surface 112 of the base 92, and a pawl 114 connected to the retainer 20a. The teeth 110 desirably have generally rectangular cross-sectional shapes, and lie in seriatim along the longitudinal axis of the base 92. The upper edge of each tooth 110 includes a chamfer 112 to facilitate the engagement of the pawl 114 with a hollow 116 formed between adjacent teeth 110, as discussed below. The longitudinal length of each tooth 110 desirably extends generally normal to the longitudinal axis of the base 92.

The pawl 114 has a shape configured to insert into and engage with the hollow 116 defined between the teeth 110. The pawl 114 preferably has a width, measured in the longitudinal direction, slightly less than that of the hollow 116.

The retainer 20a comprises an aperture 118 extending between the retainer base surface 48a and the channel bottom surface 56a. A flexible finger 120 extends from the retainer 20a in a cantilever fashion and into the retainer aperture 118. The flexible finger 120 supports the pawl 114 at its distal end. Although FIG. 8 illustrates the finger 120 as extending in the distal direction, it is contemplated that the finger 120 can alternatively extend in the proximal direction as well.

The flexible finger 120 preferably comprises a protuberance 122 which extends upwardly beyond the channel bottom surface 56a and into the central channel 44a with the finger 120 in an undeflected state. The cantilever nature of the finger 120 enables the finger 120 to deflect downward so that the protuberance 122 lies below the retainer bottom surface 56a. With the finger 120 so deflected, the pawl 114 engages the series of teeth 110. That is, the pawl 114 inserts into a hollow 116 defined between the teeth 110. The interengagement between pawl 114 and the teeth 110 prevents the retainer 20a from sliding over the base 92.

S-Clip

FIGS. 9 and 10 illustrate a catheter anchoring system 10b in accordance with a further embodiment of the present invention. Where appropriate, like numbers with an "b" suffix have been used to indicate like parts of the embodiments for ease of understanding.

The catheter anchoring system 10b is substantially identical to the anchoring system 10 first described above, with the addition of an S-clip 124 to retain a microbore or small bore tubing 126. The microbore tubing is commonly used, for example, with epidural catheterization procedures, as discussed in detail below.

The S-clip 124 comprises a generally U-shaped channel 128 defined by a pair of arcuate, upstanding walls 130 extending from a base plate 132. As best seen in FIG. 10, the S-clip 124 further comprises a plurality of retainers 134, each retainer 134 having a spherical head 136 support by a cylindrical stem 138. The stems 138 extend from the base plate 132. The retainer stems 138 are positioned from one another and from the upstanding walls 130 by a distance slightly greater than the diameter of the microbore tubing 126. The retainers 134 are also positioned such that the spherical heads 136 of the retainers 134 are positioned from one another and from the upstanding walls 130 by a distance slightly less than the microbore tubing 126. As best seen in FIG. 10, the retainer heads 136 prevent the microbore tubing 126 from disengaging from the S-clip 124 in the transverse direction once the microbore tubing 126 is snaked between the retainers 134 and the upstanding walls 130.

An adhesive attaches the base plate 132 of the S-clip 124 to base pad 16b. Alternatively, the base plate 132 may be attached to the base pad 16b by like means (e.g., embedding or otherwise weaving the base plate 132 into the base pad 16b) as well.

The components of the anchoring system 10, save the base pad 16 (i.e., the retainer 20, tube clip 24, adaptor 22, slide clamp 78, base 92 and S-clip 124), may be constructed in any of a variety of ways which will be well known to one of skill in the art. For instance, each individual component may be integrally molded such as by injection molding or by thermoplasty. The components preferably comprise a durably, flexible material, and more preferably comprise a generally inert, non-toxic material. In a preferred embodiment, the components are molded of plastic, such as, for example, polycarbonate, polyvinylchloride, polypropylene, polyurethane, tetrafluoroethylene (e.g., TEFLON®), polytetrafluoroethylene (a.k.a., PTEF), acetal resin (e.g., DELRIN®), chlorotrifluoroethylene (e.g., KELF®), nylon or like polymers.

Method of Use

The following discussion of the method of use will be with reference to FIGS. 1 and 2, and initially will be in the context of intravenous catheterization. As the following discussion will illustrate, however, it is understood that the anchoring system 10 can be used in other catheterization procedures as well. The discussion of the method of use is intended to augment the above description of the invention, and, thus, should be read together.

A nurse typically begins the catheterization process by positioning the catheter 14 at a desired location above a vein. The nurse introduces a needle or other stylus through a cannula portion of the catheter 14 and into the skin of the patient at a desired angle of incident. For intravenous use, the catheter 14 commonly has an incident angle of approximately 7°. The nurse then inserts the cannula of the catheter 14 into the patient and withdraws the needle or stylus. The catheter hub 30 remains exposed above the skin.

The nurse inserts the distal end of the adaptor 26 into the catheter hub 30. The clip 34 has been slidably mounted in a most distal position so that it does not interfere with the insertion of the adaptor distal end 26 into the catheter hub 30.

The nurse then slides the clip 34 in a proximal direction to engage the catheter hub 30. In this manually selected position, the clip 34 securely attaches the adaptor 22 to the catheter 14. The rachet teeth of the adaptor 22 cooperate with the pawl to resist distal movement of the clip 34 and to hold the clip 34 in the manually selected position.

The nurse removes the paper backing which initially covers the adhesive bottom surface 18 of the base pad 16, and attaches the pad 16 to the patient's skin proximate to the indwelling catheter 14. Specifically, the nurse grips the backing tab 67 proximate to the retainer 20. The indicia 69 on the tab 67 indicates the locate at which the nurse should grip the tab 67. The nurse then pulls on the tab 67 and peels the backing off one half of the bottom adhesive layer 18. The nurse positions the slot 68 of the pad 16 around the catheter cannula 14 with the instructing indicia 70 (e.g., indicating arrow) pointing in the direction of the catheter 14. The nurse then places the bottom layer 18 against the patient's skin to adhere the base pad 16 to the patient. Light pressure over the upper layer 64 assures good adhesion between the base pad 16 and the patient's skin. The base pad 16, due to its flexibility, conforms to the contours of the topical surface to which the base pad 16 adheres.

The nurse then repeats this procedure for the other half of the pad 16. Alternatively, the nurse may completely remove the backing from the pad 16 before attaching the pad 16 to the patient's skin.

The nurse orients the adaptor 22 with the clip 34 positioned to the side of the tubular body 25 (i.e., with the support arm 32 extending in the lateral direction) and locates the adaptor support arm 32 above the series of retainer slots 50 with the latch 36 positioned distal of the retainer distal end.

The nurse then snaps the adaptor 22 into the retainer 20 located proximal of the pad notch 68. In doing so, the adaptor 22 is pressed between the longitudinal walls 46 of the retainer 20 with the support arm 32 extending in a lateral direction. As the nurse presses the adaptor 22 into the retainer 20, the chamfered edges 58 around the slots 50 of the longitudinal wall 46 guide the support arm 32 into one of the slots 50.

As mentioned above, the opening 47 of the channel 46 has a smaller width measured in the lateral direction than the diameter of the tubular body 25. The lateral walls 46 thus deflect outwardly in a lateral direction. Once the tubular body 25 of the adaptor 22 rests within the central channel 44 of the retainer 20, the lateral walls 46 spring back to snap the adaptor 22 in place. The walls 46 of the retainer 20 thus prevent unintentional transverse and lateral movement of the adaptor 22.

In this position, the protuberance 40 of the adaptor 22 either rests either in a slot 50 or in the relief 60, proximal of the slot 50 through which the support arm 32 passes. The protuberance 40 engages a portion of the longitudinal wall 46, which forms either the relief 60 or the slot 50, to prevent the clip 34 from pivoting relative to the tubular body 25. The protuberance 40 thus ensures that the latch 36 maintains engagement with the catheter hub 30.

The slot 50 through which the support arm 32 passes prevents the adaptor 22 from sliding in the longitudinal direction. That is, the slot 50 prevents longitudinal displacement of the adaptor 22 when secured within the central channel 44.

The ergonomic design of the retainer 20 provides for a variety of positions of the adaptor 22 in the retainer 20 so that the retainer 22 is not technique or position sensitive. That is, a nurse can simply press the adaptor 22 into the retainer 20, irrespective of the side on which the support arm 32 is located, and irrespective of the position of the support arm 32 relative to a particular slot 50. So long as the support arm 32 is positioned above the series of slots 50, the chamfered edges 58 of the wall 46 will guide the support arm 32 into a slot 50. The protuberance 40 of the adaptor 22 also fits within an adjacent slot 50 or the relief 60.

With the support arm 32 extending through a slot 50 of the retainer 20, the adaptor 22 lies in a "low profile" position. That is, the support arm 32 of the adaptor 22 extends in the lateral direction to reduce the overall height of the anchoring system 10, as measured in the transverse direction. This position of the adaptor 22 reduces the risk of the system 10 interfering with surrounding action. The retainer 20, however, allows the adaptor 22 to rotate either to a position in which the support arm 32 extends in the transverse direction, or to a position 180° for the original position to locate the adaptor clip 34 on the opposite side of the retainer 20.

Once in the low profile position, the adaptor 22 will normally remain in this position until the adaptor 22 and its associated tubing 12 are removed and replaced by another.

As FIG. 1 illustrates, the nurse may also form a safety loop in the fluid supply tubing 12, as known in the art, and secure the safety loop to the patient by inserting a portion of the tubing 12 into the tube clip 24. The safety loop absorbs any tension applied to the fluid supply tube to prevent the adaptor 22 and/or catheter 14 from being pulled.

A nurse may use the slide clamp 78 to remove the adaptor body 25 from the retainer 20. The nurse inserts the tab 82 of the slide clamp 78 into the key-way groove 62 on the proximal end of the retainer 20. Because the tab 82 has a larger width than the depth of the key-way groove 62, measured in the transverse direction, the tab 62 pries the tubular body 25 from the central channel 44 as the nurse inserts the tab 82 into the key-way groove 62 in the distal direction. The nurse may further use the slide clamp 78 to leverage the proximal end of the tubular body 25 out the upper opening 47 of the retainer 20. Having displaced the proximal end of the adaptor 22 from the retainer 20, the nurse may easily remove the adaptor distal end from of the retainer 20. Alternatively, the nurse may also remove the tubular body 25 by lifting up on the tubing 12 while holding down the pad 16 or the retainer 20 with the other hand.

FIGS. 6 through 8 illustrate the catheter anchoring system 10a particularly suited for arterial catheterization. Because of the criticality of the incident angle (i.e., the angle at which the catheter 14a projects into the patient) at which the catheter 14a must be maintained, it is advantageous to precisely position the retainer 20a so that the retainer 20a holds the catheter 14a at the desired incident angle. The desired range of incident angle commonly is about 5°–30° for arterial catheterization. The incident angle preferably ranges between about 15° and about 25°, and more preferably equals about 22°.

A nurse inserts the catheter cannula 14a into an artery in a similar manner to that described above in connection with intravenous catheterization. The nurse subsequently connects the adaptor 22a to the indwelling catheter 14a as previously described. The nurse also attaches the flexible pad 16a to the patient in a like manner to that described above. If desired, the nurse can remove one of the wings 140 of the pad 16a before attaching the pad 16a to the patient, by tearing the pad 16a along the perforation line 142.

The nurse orients the adaptor 22a with the clip 34a positioned to the side of the tubular body 25a (i.e., with the support arm 32a extending in the lateral direction) and locates the adaptor support arm 32a above the series of retainer slots 50a with the latch 36a positioned distal of the retainer distal end. If the nurse positions pad 16a too close to or too far from the indwelling catheter 14a, the nurse can slide the retainer 20a in the desired direction to locate the retainer slots 50a beneath the adaptor support arm 32a.

The nurse then snaps the adaptor 22a into the retainer 20a located proximal of the pad notch 68a. In doing so, the chamfered edges 58a around the slots 50a of the longitudinal wall 46a guide the support arm 32a into one of the slots 50a. The retainer 20a automatically slides longitudinally to precisely position a corresponding slot 50a beneath the support arm 32a. The adaptor 22a thus snaps into the retainer 20a without causing the catheter 14a to move substantially.

The tubular body 25a contacts the protuberance 122 of the finger 120 and causes the finger 120 to deflect downward as the adaptor tubular body 25a snaps into the central channel 44a. In turn, the pawl 114 engages the series of teeth 110 which prevents longitudinal movement of the retainer 20a while holding the adaptor 20a. If the nurse removes the adaptor 22a—preferably by using the slide clamp tab 82a— the finger 120 springs back to its undeflected state and the retainer 20a freely slides over the rail 96. The pawl 114 normally does not engage the series of teeth 110.

The ability to precisely position the retainer 20a beneath the catheter adaptor 22a connected to the catheter 14a, enables the nurse to hold the catheter 14a in a stable position and ensures that the retainer 20a will hold the adaptor 22a, and thus the catheter 14a, at the precise incident angle. Without the ability to adjust the longitudinal position of the retainer 20a, the nurse may perform a series of position iterations before properly locating base pad 16a, and thus the retainer 20a, relative to the indwelling catheter 14a.

For epidural catheterization, an anesthesiologist, for example, inserts the distal end of microbore tubing 126 into the epidural space. The proximal end of the microbore tubing 126 conventionally includes a Toughy-Bourst adaptor 144 or other adaptor device to couple with the fluid supply tube 12b transporting the anesthesia. It is imperative that the connection between the microbore tubing 126 and the fluid supply tubing 144 remain intact, and that the distal end of the microbore tubing 126 remains in place. For if the epidural space is exposed to air-borne microbes, meningitis may develop. Thus, a secure interconnection between the microbore tubing 126 and the fluid supply 12b should exist, and the microbore tubing 126 should be isolated from any tension placed on either the fluid supply tube 12b, as well as the adaptor 22b.

FIGS. 9 and 10 illustrate the catheter anchoring system 10b particularly suited for epidural catheterization. A doctor uses the present anchoring system 10b in a manner similar to that described above in connection with intravenous catheterization, with the exceptions that doctor connects the adaptor 22b to microbore tubing 126 and adheres the base pad 16b to the patient's torso.

The doctor subsequently snakes the microbore tubing 126 through the S-clip 124 by first pressing the tubing 126 between a retainer 134 and the wall 130, and then wrapping the tubing 126 between the first and second retainers 134. Light pressure forces the tube 126 between the retainers 134. The doctor then wraps the tube 126 back between the second retainer 134 and the second wall 130, and presses the tube 126 therebetween. The S-clip 124 secures the microbore tube 126 in place and isolates the microbore tube 126 from tension placed on the adaptor 22b and/or the fluid supply tube 12b with the microbore tube 126 inserted accordingly.

Additional Embodiments

Figure 11:
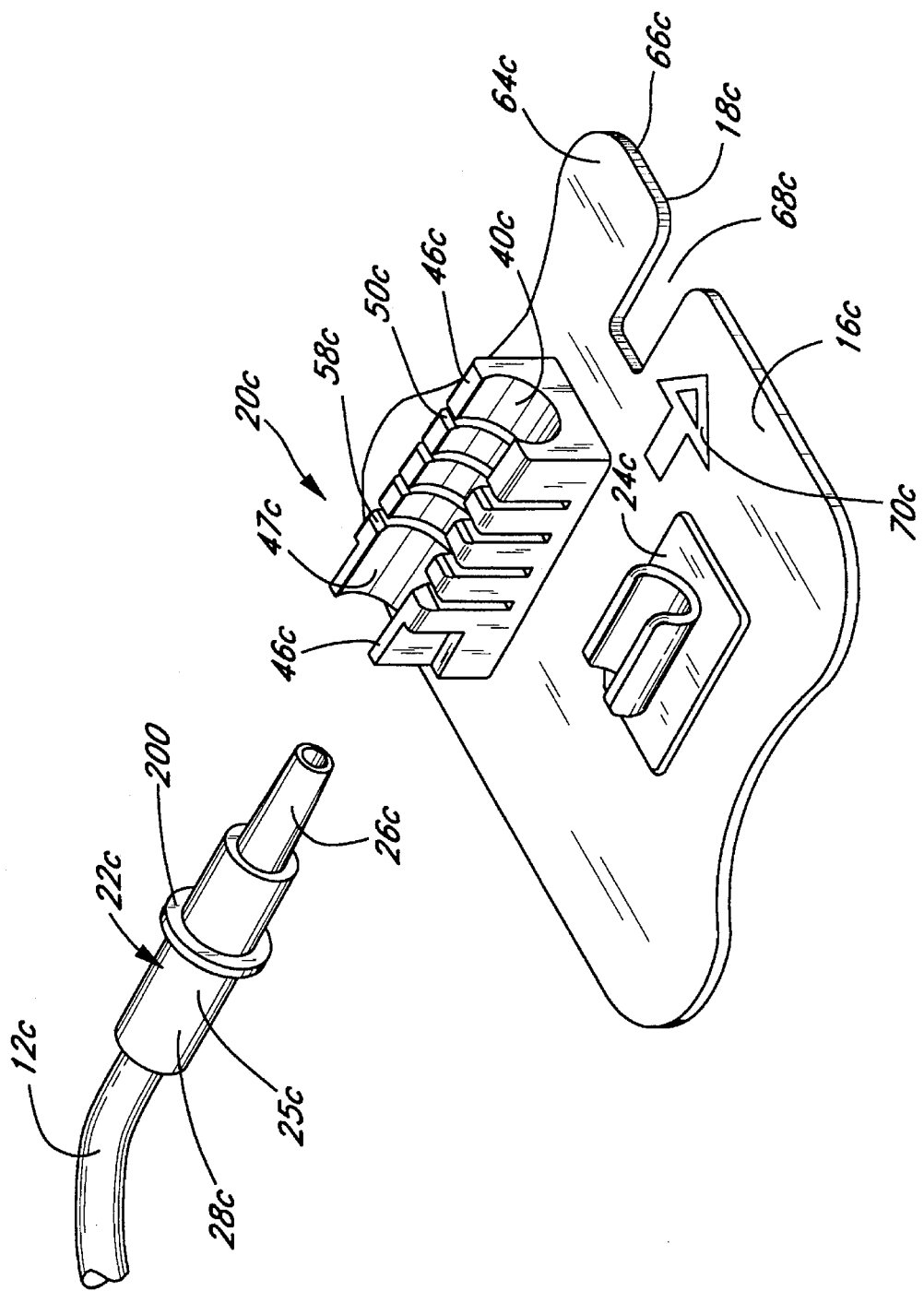
FIG. 11 is a top perspective view of a catheter anchoring system in accordance with an additional preferred embodiment of the present invention.
Figure 12:
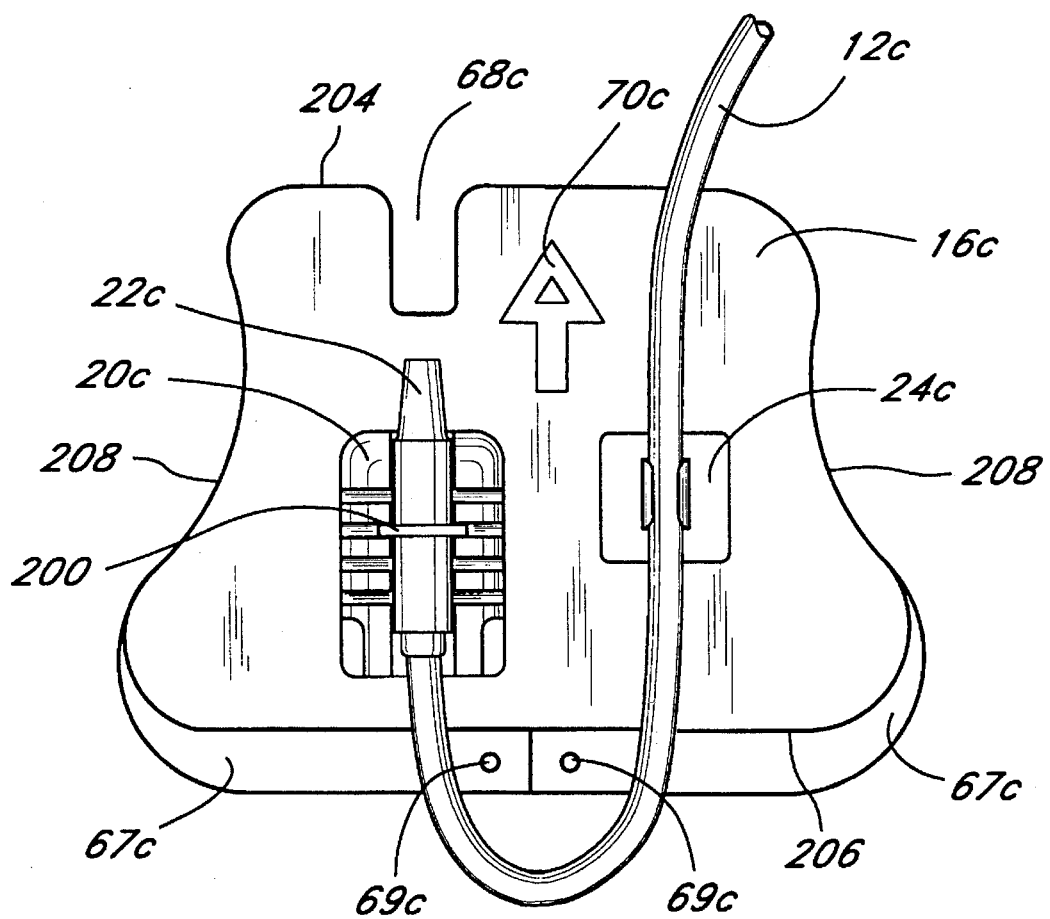
FIG. 12 is a top plan view of the catheter anchoring system of FIG. 11 illustrating an adaptor held by a retainer.

As mentioned above, it is contemplated that other types of adaptors in addition to the one disclosed above can be used as well with the present catheter anchoring system. FIGS. 11 and 12 illustrate a catheter anchoring system 10c in accordance with a further embodiment of the present invention which includes a different catheter adaptor style. Where appropriate, like numbers with a "c" suffix have been used to indicate like parts of the embodiments for ease of understanding.

Like the catheter anchoring systems described above, the present catheter anchoring system 10c principally comprises a flexible anchor pad 16c having an adhesive bottom side 18c, which attaches to the skin of the patient. The pad 16c supports a retainer 20c. The retainer 20c is configured to receive and secure in place a catheter adaptor 22c which connects to an indwelling catheter 14c. The pad 16a may also support a tube clip 24c which is used to retain a portion of the tubing 12c.

FIG. 11 illustrates the adaptor 22c as comprising a generally tubular body 25c defined between a distal end 26c and a proximal end 28c. The proximal end 28c is adapted to receive a distal end of the tube 12c. In an exemplary embodiment, at least a portion of the fluid supply tube 12c is permanently attached to the body proximal end 28c.

The distal end 26c is configured to engage a proximal end of the indwelling catheter 14c (not shown). Although FIGS. 11 and 12 illustrate the distal end 26c of the adaptor 22c as having a frusto-conical shape configured to engage a standard lure-type catheter hub 30c (not shown), it is contemplated that the distal end 26c could be configured as well to engage other types of connectors.

Figure 14:
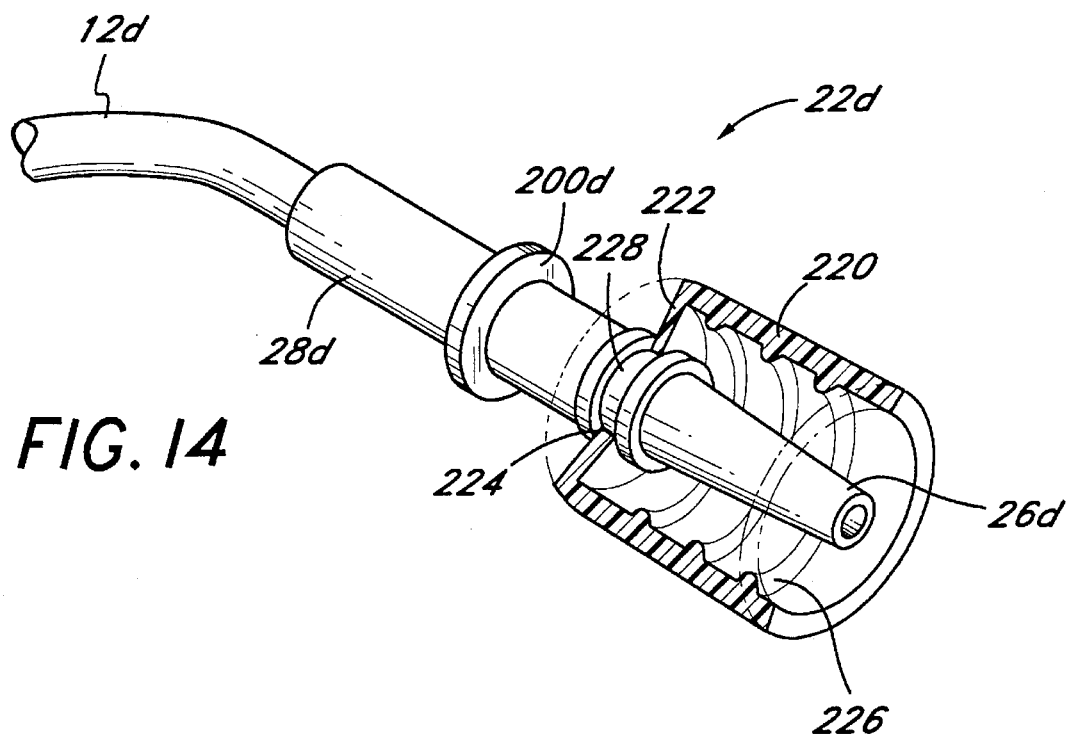
FIG. 14 is a partially sectioned perspective view of an alternative embodiment of a catheter adaptor which may be used with the anchoring system of FIG. 11.

FIG. 14 illustrates an alternative configuration of the distal end 26d of the catheter adaptor 22d. Again, for consistency, like numbers with a "d" suffix have been used to indicate like parts of the catheter adaptor of FIG. 11 and the catheter adaptor of FIG. 14.

The catheter adaptor 22d includes a standard lure-lock type fitting 220 attached to the body 25d of the catheter adaptor 22d so as to circumscribe the distal end 26d of the catheter adaptor 22d. The lure-lock fitting 220 preferably is attached in a manner which permits the fitting 220 to be rotated about the catheter adaptor body 25d. It is contemplated, however, that the distal end of the adaptor could comprise a female lure-lock type connector (i.e., a hub including nubs or threads on its external surface) as well if required by a particular application.

In the illustrated embodiment, the fitting 220 has a generally tubular shape with a closed proximal end 222. The closed end 222 includes an aperture 224 of a sufficient size to receive a portion of the adaptor body 25d, as described below. The fitting 220 includes conventional internal threads 226 in order to engage corresponding threads of a conventional female lure-lock fitting (not shown).

The adaptor body 25d desirably includes an annular groove 228 which receives a portion of the closed end 222 of the fitting 220 to interconnect the fitting 220 and the adaptor body 25d. This interconnection also permits the fitting 220 to be rotated about the adaptor body 25d.

To assemble the catheter adaptor 22d, the conical shaped distal end 26d of the body 25d is inserted into the aperture 224 of fitting closed end 222. The body 25d is then forced into the fitting 220 to slightly deflect the closed end 222 until the closed end 222 snaps into the annular groove 228 of the body 25d. In this position, the body 25d captures a portion of the fitting 220 to couple these elements together.

With reference to FIG. 11, the adaptor 22c includes at least one annular collar 200 interposed between the proximal and distal ends 28c, 26c of the tubular body 25c. The adaptor 22d of FIG. 14 also includes a like annular collar 200d. It is contemplated that the collar 200 of the adaptor 22c of FIG. 11 and the collar 200d of the adaptor 22d of FIG. 14 will be substantially identical, and, thus, the description herein will be understood as applying equally to both embodiments.

The annular collar 200 flares radially outwardly and circumscribes the tubular body 25c. The annular collar 200 has a thickness measured in a longitudinal direction which is slightly less than a width of a slot 50c in a retainer wall 46c so that the collar 200 fits within the slot 50c of a retainer wall 46c, as discussed in detail below.

The adaptor 22c is preferably formed of a durable, biocompatible plastic material. The adaptor 22c more preferably is formed of clear plastic so a nurse can see bubbles or backflow through the adaptor 22c. In an exemplary embodiment, the adaptor is formed of polycarbonate by injection molded; however, those skilled in the art will readily appreciate that the adaptor can be formed by other construction methods known in the art.

FIGS. 11 and 12 also illustrate the retainer 20c which is substantially identical to the retainer 20 described above. The retainer 20c comprises a central channel 44c interposed between a pair of opposing longitudinal walls 46c. The central channel 44c extends through the retainer 20c along an axis which is generally parallel to a longitudinal axis of the retainer 20c.

The central channel axis 44c has a generally circular cross-sectional shape which is truncated at an upper end to form an opening 47c. The central body 44c has a diameter sized to receive the tubular body 25c of the catheter adaptor 22c. In a preferred embodiment, the diameter of the central channel 44c generally matches that of the tubular body 25c.

In cross section, the central channel 44c extends through an arc greater than 180° about the channel axis such that the lateral length of the opening 47c is less than the diameter of the central channel 44c. In an exemplary embodiment, the cross-sectional shape of the central channel 44c extends through an arc of about 200° about the channel axis.

Figure 13A:
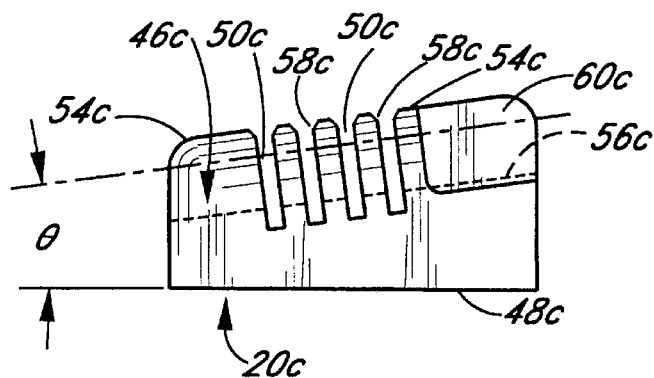
FIG. 13a is a side elevational view of the retainer of FIG. 12.

As best seen in FIG. 13a, the channel axis is desirably skewed relative to a base surface 48c of the retainer 20c. An incident angle θ formed between the base surface 48c and the channel axis is less than 45°. The incident angle θ desirably ranges between 5° and 30°. In an exemplary embodiment for intravenous use, the angle θ preferably approximately equals 7°.

The longitudinal walls 46c are substantially identical. Each wall 46c has a thickness measured in the lateral direction less than the length of the support arm 32 of the adaptor 22, as it is desirable for the present retainer 20c to accept both the above-described adaptor 22 which comprises a support arm 32 connected to a clip 34, as well as the present adaptor 22c which comprises an annular collar 200. Preferably, the thickness of the wall 46c measured in the lateral direction is greater than the distance measured radially by which the collar 200 extends beyond the exterior surface of the tubular body 25c (i.e., a radial height). The length of each wall 46c, as measured in the longitudinal direction, is preferably coextensive with the length of the retainer 20c.

Each wall 46c comprises a uniform series of slot 50c. The series comprises at least two (2) slots 50c and not more than twenty (20) slots 50c. More preferably, the series comprises less than seven (7) slots 50c. In an exemplary embodiment, as illustrated in the figures, the series comprises four (4) slots 50c.

As discussed above, each slot 50c is sized to receive the collar 200 of the adaptor 22c, as well as the support arm 32 of the catheter adaptor 22, to prevent longitudinal displacement of the respective adaptor 22, 22c. Each slot 50c desirably has a rectangular shape. As seen in FIG. 12, the slots 50c extend from an exterior surface 52c, through the wall 46c, and open into the central channel 44c. The width of the slot 50c, as measured in the longitudinal direction, is desirably slightly greater than the width of the support arm 32 and the width of the collar 200.

Figure 13B:
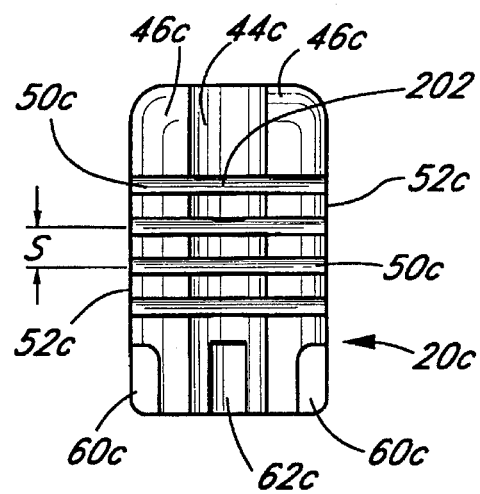
FIG. 13b is a top plan view of the retainer of FIG. 12.

As illustrated by FIG. 13a, each slot 50c extends in the transverse direction from an upper edge 54c of the longitudinal wall 46c to a point below the bottom 56c of the central channel 44c. The height of the slot 50c, as measured in the transverse direction, is thus greater than the distance between the upper edge 54c and the channel bottom 56c of the retainer 20c. As seen in FIG. 13b, the retainer 20c further includes a series of lateral grooves 202 which extend between opposing slots 50c and extend into the retainer 20c from the channel bottom surface 56c. The opposing slots 50c and groove 202 thus form a lateral channel which extends through the retainer 20c in the lateral direction and cuts into the retainer 20c from the upper edge 54c to a point below the channel bottom surface 56c. The groove 202 desirably is sized to receive a portion of the collar 200 such that with the tubular body 25c positioned within the central channel 44c, the collar 200 extends between opposing slots 50c and into the groove 202. Thus, the groove 202 has a depth, measured between the lower surface 56c of the central channel 44c and the bottom of the groove in transverse direction, which is greater than the radial height of the annular collar 200.

FIG. 13b illustrates that the spacing S between the slots 50c, on center, desirably equals about half the distal L (see FIG. 2) between the support arm 32 and the protuberance 40 of the catheter adaptor 22. The position of the slots in relation to the proximal and distal ends 26c, 28c of the retainer 20c is desirably configured in accordance with the spacing and positioning discussed above in connection with the above-described retainer 22, such that the present retainer 22c can be used with the above-described adaptor 22, including a clip 34.

FIGS. 11 and 13a illustrate the upper edge of each longitudinal wall 46c which comprises a series of chamfers 58c formed and positioned as disclosed above in connection with the retainer 20. As discussed above, the chamfers 58c slope downwardly towards the slot 50c to facilitate the insertion of either the support arm 32 of the above-described catheter adaptor 22 or the annular collar 200 of the present catheter adaptor 22c into the slot 50c.

As FIGS. 11–13b illustrate, each longitudinal wall 46c may further comprise a relief 60c disposed on the proximal end of the retainer 20c. The configuration and position of the relief 60c desirably is in accordance with the above description of the retainer 20. FIG. 11 further illustrates that the retainer 20c may additionally comprise a key-way groove 62c to facilitate removal of the catheter adaptor 22c from the retainer 20c, as discussed above. The key-way groove 62c desirably is also positioned and configured in accordance with the above disclosure in connection with the retainer 20.

The retainer 20c is made of relatively stiff plastic material, but is somewhat flexible such that the adaptor 22c forces the upper edges 54c of the longitudinal walls 46c outwardly when a nurse presses the adaptor 22c into the central channel 44c of the retainer 20c. The retainer 20c is desirably formed of polycarbonate by injection molding. When the adaptor 22c sits within the central channel 44c, the upper edges 54c of the walls 46c snap inwardly to their original position to securely hold the adaptor 22c within the retainer 20c.

An adhesive preferably attaches the retainer 20c to the anchor pad 16c. Alternatively, the retainer 20c may be attached to the anchor pad 16c by like means as well, e.g., embedding or otherwise weaving the retainer into the anchor pad 16c.

FIG. 11 illustrates the anchor pad 16c as comprising a flexible, laminate structure comprising an upper paper or other woven or non-woven cloth layer 64c and a bottom adhesive layer 18c, with an inner cellulose foam layer 66c interposed therebetween. Alternatively, the flexible base pad 16 may comprise an adhesive bottom layer 18 and an upper cellulose foam layer. An upper surface of the foam layer is roughened by corona treating with a low electric charge, as known in the art. The foam layer 66c forms a cushion between the patient's skin and the rigid, plastic retainer 20c and tube clamp 24c. The adhesive layer 18c may comprise a coating of diaphoretic or nondiaphoretic material, depending upon the patient's skin condition. A medical grade foam tape with a diaphoretic or a nondiaphoretic adhesive is available commercially from NDM Manufacturers.

The removable paper or plastic backing (not shown) desirably covers the bottom adhesive layer 18 before use. As discussed above and illustrated in FIG. 12, the backing is preferably divided into a plurality of piece and includes tabs 67c to ease removal of the backing from the pad 16. The tabs 67c may include indicia 69c (e.g., dots, text, arrows, etc.) to indicate the location at which to grip the corresponding tab 67c when peeling the removable backing off the pad 16c.

As best seen in FIG. 12, the anchor pad 16 desirably has a generally trapezoidal shape with rounded corners. A distal edge 206 of the anchor pad 16c desirably has a width, as measured in the lateral direction, wider than that of a proximal edge 204. The longer distal edge 206 provides a longer adhesive surface over a rough contact surface, such as, for example, over knuckles, vertebrae, or the like. The generally trapezoidal shape, however, minimizes the overall size of the anchor pad 16c attached to the patient. The trapezoidal shape also provides the same surface area as a square pad with a appearance of a smaller pad. The longitudinal sides 208 of the anchor pad 16c preferably taper from the proximal edge 206 to the distal edge 204, and more desirably have concave shapes.

The anchor pad includes a notch 68c positioned along the proximal edge 204 of the anchor pad 16c and adjacent to the point of insertion of the catheter cannula. Preferably, the notch 68c is symmetrically positioned about the channel axis 44c of the retainer 20c attached to the anchor pad 16c. The notch 68c is sized to permit visual inspection of the catheterized site and is large enough to allow for variable placement of the pad 16c with respect to the insertion site. That is, the notch 68c is large enough that a nurse is not required to precisely position the pad on the patient's skin with respect to the indwelling catheter 14c (not shown).

As seen in FIGS. 11 and 12, the anchor pad 16c desirably may comprise indicia 70c sometimes in the form of an arrow which indicates the proper orientation of the anchor pad 16 in reference to the catheterized site. When properly used, the indicia 70c points toward the indwelling catheter 14c (not shown).

The anchor pad 16c preferably supports a clip 24c which secures the fluid supply tube 12c to the anchor pad 16c. As seen in FIG. 12, the fluid supply tube 12c is preferably looped back around in a proximal direction and inserted into the clip 24c to form a safety loop, as known in the art. The tube clip 24c is desirably configured in accordance with the above description. The clip 24c may be made in a variety of sizes to accommodate various calibers of fluid flow tubing 12c.

In use, a nurse typically uses the catheter anchoring system 10c in connection with an indwelling catheter 14c (not shown). The catheter 14c is inserted into a body lumen, such as a vein, in accordance with the above description. The nurse then inserts the distal end 26c of the adaptor 22c into a catheter hub 30c (not shown) to connect the adaptor 22c to the catheter 14c. The nurse may then secure the adapter 22c to the catheter 14c by means of the ratchet clip, or the lure-lock fitting.

The nurse removes the paper backing which initially covers the adhesive bottom surface 18c of the anchor pad 16c, as described above, and attaches the anchor pad 16c to the patient's skin proximate to the indwelling catheter 14c. The nurse specifically positions the notch 68c of the pad 16c around the catheter cannula 14c with the indicating arrow 70c pointing in the direction of the catheter 14c. The nurse generally aligns the proximal edge 204 of the anchor pad 16c with the insertion site.

The nurse positions the adaptor 22c above the series of retainer slots 50c, and snaps the adaptor 22c into the retainer 20c. In doing so, the adaptor 22c is pressed between the longitudinal walls 46c of the retainer 20c with the annular collar 200 extending into opposing slots 50c and into the corresponding groove 202 of the retainer 20c. As the nurse presses the adaptor into the retainer 20c, the chamfered edges 58c around the slots 50c of the longitudinal walls 46c guide the annular collar 200 into the slots 50c. The retainer 20c secures the adaptor 20c as described above.

With the annular collar 200 positioned in the opposing slots 50c the adaptor 22c is prevented from sliding in a longitudinal direction.

Like the above-described embodiments of the retainer, the ergonomic design of the retainer 20c provides for various positions of the adaptor 22c in the retainer 20c so that the retainer 22c is not technique- or position-sensitive. That is, a nurse can simply press the adaptor 22c into the retainer 20c, irrespective of the position of the annular collar 20 relative to a particular slot 50c of the retainer 20c. So long as the annular collar 200 is positioned above the series of slots 50c, the chamfered edges 58c of the wall 46c will guide the annular collar 200 into the slot 50c.

The present embodiment of the retainer 20c, as mentioned above, may also be used with the above-described adaptor 22 having the clip 34. A nurse uses the present retainer with the above-described adaptor 22 in the same manner as described above in connection with the above-described retainer 20.

If the catheter hub 30 (see FIG. 1) is a standard female lure-lock fitting, the lure-lock fitting 220 (FIG. 14) of the adaptor body 22d is rotated with the distal end 26d inserted into the catheter hub 30 to interlock the corresponding fittings 222, 30 in the known manner. The catheter adaptor 22d is then used with the anchoring system in a like manner to that described above.

Although this invention has been described in terms of certain preferred embodiments, other embodiments apparent to those of ordinary skill in the art are also within the scope of this invention. Accordingly, the scope of the invention is intended to be defined only by the claims which follow.

What is claimed is:

1. An anchoring system for securing an indwelling catheter within a body lumen of a patient and for securely interconnecting the indwelling catheter with a tube, said catheter of the type having a proximal end including a lure-lock connector, said anchoring system comprising:

an adaptor having a generally tubular body with a distal end which is configured to engage the proximal end of the catheter, said distal end including a lure-lock connector which is adapted to engage the corresponding lure-lock connector of the catheter proximal end, said adaptor additionally comprising a radially extending member which projects from an exterior surface of said tubular body in a radial direction at a point distanced from said lure-lock connector of said adaptor distal end; and a retainer comprising a channel configured to receive said tubular body of said adaptor, said retainer additionally comprising a series of lateral slots sized to receive and to capture said radially extending member of said adaptor with said adaptor positioned within said channel of said retainer so as to prevent said adaptor from sliding within said channel, whereby said series of slots provide multiple positions along said channel where said retainer can receive said radially extending member of said adaptor.

2. The anchoring system of claim 1, wherein said radially extending member comprises an annular collar which circumscribes said tubular body.

3. The anchoring system of claim 1, wherein said lure-lock connector comprises a tubular member positioned about said distal end of said adaptor, said tubular member including an internal thread and being attached to said distal end of said adaptor body in a manner allowing said tubular member to move relative to said adaptor distal end.

4. The anchoring system of claim 1, wherein said distal end of said adaptor is configured to engage a hub positioned on the proximal end of the catheter.

5. The anchoring system of claim 1, wherein said lure-lock connector comprises at least a portion of a thread which is adapted to engage a corresponding thread portion of the corresponding lure-lock connector on the proximal end of the catheter.

6. The anchoring system of claim 1, wherein at least one lateral slot of said retainer is spaced from a distal end of said retainer by a distance that is substantially equal to the distance between said radially projecting member and said lure-lock connector of said adaptor.

7. The anchoring system of claim 1 additionally comprising a flexible anchoring pad comprising an adhesive bottom surface which attaches to the patient's skin, said anchoring pad supporting said retainer.

8. The anchoring system of claim 7 additionally comprising a tube clip configured to receive a portion of a tube attached to said adaptor, said tube clip being supported by said anchor pad.

9. The anchoring system of claim 1, wherein said longitudinal channel has a truncated circular cross-sectional shape which extends through an arc of greater than about 180°.

10. A method of anchoring an indwelling catheter/tube interconnection to a patient, comprising the steps of:

providing an adaptor having a generally tubular body with a radially extending member and a distal end which is adapted to engage a lure-lock fitting at a proximal end of the catheter;

providing an anchor pad with an adhesive back, said anchor pad supporting a retainer configured to securely receive said adaptor, said retainer comprising a central channel and a series of lateral slots, whereby said series of slots provide multiple positions along a longitudinal axis of said retainer where said retainer can receive said radially extending member of said adaptor;

adhering said anchor pad to a patient's skin proximate to said indwelling catheter;

inserting the distal end of the adaptor into the proximal end of the catheter to join the adaptor distal end with the proximal end of the catheter;

rotating the lure-lock fitting about the joined ends of the adaptor and catheter to interlock the joined ends;

positioning said radially extending member above said series of lateral slots; and inserting said adaptor tubular body into said channel with the radially extending member slipping into one slot of said series of slots.

\* \* \* \* \*

UNITED STATES PATENT AND TRADEMARK OFFICE
CERTIFICATE OF CORRECTION

PATENT NO. : 5,578,013
DATED : November 26, 1996
INVENTOR(S) : Steven F. Bierman It is certified that error appears in the above-indentified patent and that said Letters Patent is hereby corrected as shown below:

In Column 8, Line 49, replace "approximately 70." with --approximately 7°.--.

Signed and Sealed this

Sixteenth Day of September, 1997

Attest:

BRUCE LEHMAN

Attesting Officer        Commissioner of Patents and Trademarks